United States Patent
Cheetham et al.

(10) Patent No.: US 11,123,279 B2
(45) Date of Patent: Sep. 21, 2021

(54) COSMETIC COMPOSITION AND THE USE THEREOF FOR REGULATING SKIN QUALITY

(71) Applicant: AchromaZ Pte. Ltd., Singapore (SG)

(72) Inventors: Peter Samuel James Cheetham, Dursley (GB); Christoph Langwallner, Singapore (SG); Margit Langwallner, Singapore (SG); Wen Jue Amelia Tan, Singapore (SG)

(73) Assignee: AchromaZ Pte. Ltd., Singapore (SG)

(*) Notice: Subject to any disclaimer, the term of this patent is extended or adjusted under 35 U.S.C. 154(b) by 0 days.

(21) Appl. No.: 16/070,590

(22) PCT Filed: Jan. 19, 2017

(86) PCT No.: PCT/SG2017/050030
§ 371 (c)(1),
(2) Date: Jul. 17, 2018

(87) PCT Pub. No.: WO2017/127025
PCT Pub. Date: Jul. 27, 2017

(65) Prior Publication Data
US 2019/0021974 A1 Jan. 24, 2019

(30) Foreign Application Priority Data
Jan. 19, 2016 (SG) ............ 10201600391R

(51) Int. Cl.
| | | |
|---|---|---|
| A61K 8/49 | (2006.01) | |
| A61Q 19/02 | (2006.01) | |
| A61Q 19/08 | (2006.01) | |
| A61K 8/55 | (2006.01) | |
| A61K 31/708 | (2006.01) | |

(Continued)

(52) U.S. Cl.
CPC ............ *A61K 8/4953* (2013.01); *A61K 8/49* (2013.01); *A61K 8/492* (2013.01); *A61K 8/498* (2013.01); *A61K 8/4973* (2013.01); *A61K 8/55* (2013.01); *A61K 31/12* (2013.01); *A61K 31/122* (2013.01); *A61K 31/166* (2013.01); *A61K 31/192* (2013.01); *A61K 31/194* (2013.01); *A61K 31/215* (2013.01); *A61K 31/216* (2013.01); *A61K 31/222* (2013.01); *A61K 31/341* (2013.01); *A61K 31/343* (2013.01); *A61K 31/351* (2013.01); *A61K 31/4035* (2013.01); *A61K 31/425* (2013.01); *A61K 31/4412* (2013.01); *A61K 31/513* (2013.01); *A61K 31/52* (2013.01); *A61K 31/522* (2013.01); *A61K 31/536* (2013.01); *A61K 31/54* (2013.01); *A61K 31/708* (2013.01); *A61Q 19/02* (2013.01); *A61Q 19/08* (2013.01); *A61K 8/9728* (2017.08); *A61K 2800/74* (2013.01)

(58) Field of Classification Search
CPC .... A61K 8/4953; A61K 31/708; A61K 31/52; A61K 8/49; A61K 8/492; A61Q 19/02; A61P 17/00
See application file for complete search history.

(56) References Cited

U.S. PATENT DOCUMENTS

| | | |
|---|---|---|
| 4,990,330 A | 2/1991 | Oyama |
| 5,164,185 A | 11/1992 | Charpin et al. |

(Continued)

FOREIGN PATENT DOCUMENTS

| | | |
|---|---|---|
| CN | 105106101 | 12/2015 |
| DE | 102004050563 | 4/2006 |

(Continued)

OTHER PUBLICATIONS

"Mint" (Database GNPD "Mint Lip Protector SPF 4", Database accession No. 1925308, Nov. 1, 2012) (Year: 2012).*
Machine translation of WO 00/38648. Accessed Dec. 4, 2019, pp. 1-2 (Year: 2019).*
Wind, C.M. et al. "Determination of in vitro synergy for dual antimicrobial therapyagainst resistant Neisseria gonorrhoeae using Etest and agar dilution" International Journal of Antimicrobial Agents 45 (2015) 305-308 (Year: 2015).*
Eve Fresh [retrieved from internet on Feb. 23, 2017] <URL: https://www.saralhealth.com/dr-jrks-eve-fresh-cream-25-gm> published on Mar. 25, 2015 as per Wayback Machine.

(Continued)

*Primary Examiner* — Andrew S Rosenthal
(74) *Attorney, Agent, or Firm* — Hamilton, Brook, Smith & Reynolds, P.C.

(57) ABSTRACT

The present invention relates to cosmetic or personal care compositions comprising two or more compounds, each compound containing an allylic or partially allylic carbonylsubstructure having the following structure I: wherein Y is a second substructure immediately adjacent to the allylic or partially allyliccarbonyl substructure and is selected from one of the following groups consisting of (i) hydroxyl-based group including —OH or —C(=)—(OH); (ii)carbonyl-based group including —C(=)—C (=O)—CH$_3$; (iii) N ether group, —O—; (iv) sultam group, —N(H)—S(=O)$_2$—; (v) lactam group, —N(H)—C(=O)—; (vi) apolar group including cyclic structures based on menthol or carotenoids; (vii) secondary aldimine containing group including —N(H)—C(NH$_2$)=N— or —N(H)—C(H)=N—; (viii) amine group, —NH$_2$; (ix) secondary amine-based group, —N(H)—; and (x) amide-based group including —N(H)—C(=O)— or —N(H)—C(=O)—N(H)—, their derivatives, isomers, salts and/or combination thereof; and a cosmetically acceptable vehicle.

(I)

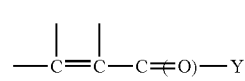

11 Claims, 7 Drawing Sheets

(51) Int. Cl.
| | | |
|---|---|---|
| A61K 31/52 | (2006.01) | |
| A61K 31/351 | (2006.01) | |
| A61K 31/341 | (2006.01) | |
| A61K 31/216 | (2006.01) | |
| A61K 31/192 | (2006.01) | |
| A61K 31/425 | (2006.01) | |
| A61K 31/222 | (2006.01) | |
| A61K 31/194 | (2006.01) | |
| A61K 31/54 | (2006.01) | |
| A61K 31/4035 | (2006.01) | |
| A61K 31/12 | (2006.01) | |
| A61K 31/536 | (2006.01) | |
| A61K 31/166 | (2006.01) | |
| A61K 31/513 | (2006.01) | |
| A61K 31/343 | (2006.01) | |
| A61K 31/122 | (2006.01) | |
| A61K 31/215 | (2006.01) | |
| A61K 31/522 | (2006.01) | |
| A61K 31/4412 | (2006.01) | |
| A61K 8/9728 | (2017.01) | |

(56) References Cited

U.S. PATENT DOCUMENTS

| | | | |
|---|---|---|---|
| 6,365,137 | B1 | 4/2002 | Aust et al. |
| 7,704,530 | B2 * | 4/2010 | Nakamura ............ A61K 8/0208 424/618 |
| 2003/0157176 | A1 | 8/2003 | Nakamura et al. |
| 2004/0081672 | A1 | 4/2004 | Gupta |
| 2004/0016143 | A1 | 8/2004 | Gupta |
| 2004/0166069 | A1 | 8/2004 | Gupta |
| 2005/0214332 | A1 | 9/2005 | Osborne et al. |
| 2006/0110341 | A1 | 5/2006 | Harichian et al. |
| 2006/0216254 | A1 | 9/2006 | Majmudar et al. |
| 2007/0009474 | A1 | 1/2007 | Xie et al. |
| 2007/0166251 | A1 | 7/2007 | Dayan et al. |
| 2008/0181920 | A1 | 7/2008 | Buerger et al. |
| 2008/0287533 | A1 | 11/2008 | Gupta |
| 2009/0028969 | A1 | 1/2009 | Sene et al. |
| 2010/0204204 | A1 | 8/2010 | Zaworotko et al. |
| 2012/0027706 | A1 | 2/2012 | Shapiro et al. |
| 2012/0082631 | A1 * | 4/2012 | Bradshaw ............... A61K 8/498 424/55 |
| 2012/0001775 | A1 | 7/2012 | Mehta et al. |
| 2012/0220545 | A1 | 8/2012 | Orlow et al. |
| 2013/0129651 | A1 | 5/2013 | Miyake et al. |
| 2014/0179747 | A1 | 6/2014 | Lewis, II et al. |
| 2014/0002273 | A1 | 8/2014 | Drapeau et al. |

FOREIGN PATENT DOCUMENTS

| | | | | |
|---|---|---|---|---|
| JP | | 61109716 A | 5/1986 | |
| JP | | H07-157495 | 6/1995 | |
| JP | | 2002193737 | 7/2002 | |
| JP | | 2004284999 | 10/2004 | |
| JP | | 2006016343 A | 1/2006 | |
| JP | | 2006342120 A | 12/2006 | |
| JP | | 2012097034 A | 5/2012 | |
| JP | | 2014114291 | 6/2014 | |
| JP | | 2015059119 | 3/2015 | |
| JP | | 2015205913 A | 11/2015 | |
| WO | | WO 00/38648 | 6/2000 | |
| WO | | WO-0038648 A1 * | 7/2000 | ............ A61Q 19/02 |
| WO | | WO 00/47045 | 8/2000 | |
| WO | | WO 00/47179 | 8/2000 | |
| WO | | WO 00/69408 | 11/2000 | |
| WO | | WO-0069408 A1 * | 11/2000 | ............ A61Q 19/00 |
| WO | | WO 01/17497 A1 | 3/2001 | |
| WO | | WO 03/051325 A1 | 6/2003 | |
| WO | | WO-03051325 A1 * | 6/2003 | .......... C07D 309/16 |
| WO | | WO 2014/160690 A1 | 10/2014 | |
| WO | | WO 2014/170239 A1 | 10/2014 | |

OTHER PUBLICATIONS

Hamdi, O.A.A., et al., "Cytotoxic Constituents from the Rhizomes of *Curcuma zedoaria*". *The Scientific World Journal*, 2014, vol. 2014, Article ID 321943, 11 Pages.

Hamman, J.H, "Composition and Applications of *Aloe vera* Leaf Gel". *Molecules*, 2008, vol. 13, pp. 1599-1616.

Kahn, V. "Multiple Effects ofMaltol and Kojic Acid on Enzymatic Browning". *ACS Symposium Series*, 1995, vol. 600, Chapter 22, pp. 277-294.

Kim, K. "Effect of ginseng and ginsenosides on melanogenesis and their mechanism of action". *Journal of Ginseng Research*, 2015, vol. 39, pp. 1-6.

Krishnamoorthy, J.R., et al., "Extract combinations of *Curcuma zedoaria* and *Aloe vera* inhibit melanin synthesis and dendrite formation in murine melanoma cells". *Journal of Applied Cosmetology*, 2010, vol. 28, pp. 103-108.

Sato, K., et al., "Down-Regulation ofTyrosinase Expression by Acetylsalicylic Acid in Murine B16 Melanoma". *Biological & Phannaceutical Bulletin*, 2008, vol. 31, No. 1, pp. 33-37.

Zhu, W. and Gao, J. "The Use of Botanical Extracts as Topical Skin-Lightening Agents for the Improvement of Skin Pigmentation Disorders". *Journal ofJnvestigative Dennatology Symposium Proceedings*, 2008, vol. 13, pp. 20-24.

International Preliminary Report on Patentability for International Application No. PCT/SG2017/050030, "A Cosmetic Composition and the Use Thereof for Regulating Skin Quality" dated Mar. 5, 2018.

International Search Report for International Application No. PCT/SG2017/050030, "A Cosmetic Composition and the Use Thereof for Regulating Skin Quality" dated Apr. 6, 2017.

Written Opinion for International Application No. PCT/SG2017/050030, "A Cosmetic Composition and the Use Thereof for Regulating Skin Quality" dated Apr. 6, 2017.

Database GNPD "Repairing Hand & Nail Cream Night & Day", Database accession No. 3703613 (Dec. 1, 2015.

Database GNPD "Mint Lip Protector SPF 4", Database accession No. 1925308 (Nov. 1, 2012).

European Search Report for EP Application No. 17741744, "A Cosmetic Composition and the Use Thereof for Regulating Skin Quality", dated Sep. 13, 2019.

\* cited by examiner

COSMETIC COMPOSITION AND THE USE THEREOF FOR REGULATING SKIN QUALITY

RELATED APPLICATIONS

This application is the U.S. National Stage of International Application No. PCT/SG2017/050030, filed Jan. 19, 2017, which designates the U.S., published in English, and claims priority under 35 U.S.C. § 119 or 365(c) to Singapore Application No. 10201600391R, filed Jan. 19, 2016. The entire teachings of the above applications are incorporated herein by reference.

FIELD OF THE INVENTION

The present invention relates to cosmetic compositions and methods for regulating skin quality.

BACKGROUND

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Cosmetics and personal care products that lighten the skin are important in many countries worldwide, and especially in Asia. Skin lightening products work by preventing the darkening of the skin due to the action of sunlight and by endogenous hormones. Skin tanning and darkening is due to the formation of melanin in melanocyte cells in the dermis layer of the skin by a metabolic pathway that begins with phenylalanine and then tyrosine, and is transferred in the form of melanosomes into keratinocytes that migrate into the epidermis to provide protection against ultraviolet (UV) light to the cells below them. A range of melanins can be produced which vary in colour from individual to individual depending on their genetics and exposure to sunlight. There are two general types, eumelanins that are black-brown, and then pheomelanins that are brown-red or even lighter in colour that are formed by the incorporation of cysteine and sometimes other compounds such as glutathione and cysteine into the melanin polymer.

The melanogenesis metabolic pathway takes place in melanocyte cells and begins with tyrosine that is converted into dopaquinone via L-3, 4-dihydroxyphenylalanine (L-dopa) by the cresolase and then catecholase activities of the enzyme tyrosinase. Dopaquinone then reacts in two ways, either incorporating cysteine or glutathione to form cysteinyldopa for example, that lead to the formation of pheomelanins, or dopaquinone is converted into dihydroxyindole carboxylic acid (DH ICA or leucodopachrome) by tyrosinase-like protein 2 (TLP2-DHICA isomerase or tautomerase). DHICA then reacts with tyrosinase-like protein 1 (TLP1-DHICA oxidase) to form dopachrome, which then spontaneously decarboxylates forming dihydroxyindole, and is then oxidised into 5,6-dihydroxyquinolone. These various indoles polymerise to form melanins of various forms depending on the various indole intermediates produced as mentioned above.

Skin lighteners can work at various stages in this pathway. One of the most common sites of action of skin lighteners is the inhibition of the tyrosinase enzyme that converts tyrosine into L-dopa. Commonly used skin lightener active ingredients of cosmetics include kojic acid (KA), which inhibits tyrosinase, and possibly other tyrosinase-like proteins that act at subsequent stages in the melanogenesis pathway. Other skin lightener active ingredients have different mechanisms of action, for instance niacinamide inhibits the transfer of melanin from melanosomes to keratinocytes, and alpha- and beta-arbutins that are glycosides of hydroquinone which has a bleaching action on the melanin itself.

Another approach to achieving skin lightening is to use materials that affect the signalling pathways that control melanogenesis. A number of signalling pathways have been identified such as involving compounds such as nitric oxide that activates guanylate kinase to produce cyclic guanosine monophosphate (cGMP) that stimulates melanogenesis, and diacylglycerides that are formed by UV radiation and that activate protein kinase C β (PKC beta) which phosphorylates and thereby activates tyrosinase.

The melanogenesis metabolic pathway is initiated in two main ways, either endogenously or UV-initiated. In the former the pituitary gland produces alpha-melanocyte stimulating hormone (α-MSH) by the selective cleavage of the precursor peptides pro-opiomelanocortin (POMC) and then adrenocorticotropic hormone (ACTH). α-MSH and ACTH bind to the melanocortin receptor 1 (MC1-R), which is located at the surface of the membrane of the melanocyte, which activates adenylyl cyclase to produce cyclic adenosine monophosphate (cAMP) which activates protein kinase A to activate the transcription factor, cAMP response element-binding protein (CREB), and to stimulate the microphthalmia-associated transcription factor (MITF) that in turn stimulates the synthesis of the tyrosinase and other proteins involved in the production of melanin as well as the Rab27a gene and the production of the melanophilin protein that is involved in the transport of melanin in the form of melanosomes along the dendrites of the melanocyte, from which it is transferred into keratinocytes by phagocytosis, a process that is controlled by the G protein coupled receptor (GPCR) protease-activated receptor 2 (PAR-2).

The role of MC1-R in melanogenesis is complex. In the absence of stimulation by α-MSH it tends to produce pheomelanins, and there appears to be considerable heterogeneity in the MC1-Rs present in different people also resulting in the formation of different melanins and thus the possession of skins of different tones and degrees of darkness and lightness.

Another way in which melanogenesis is initiated is by the UV photons in sunlight. These have three main effects. UV generates singlet oxygen, a highly reactive form of dioxygen, in the skin, especially via photosensitisers on the skin such as porphyrins. Also UVB in particular damages DNA in skin cells and as a result excision repair produces dimeric degradation products of the pyrimidine base thymine. Two main types are formed, the most common being cyclobutane dimers (CBDs) together with less numerous but reportedly more active 6,4-photoproducts, both of which contain a common amide based substructure —C(=O)—NH—C(=O)—,

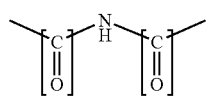

and with CBD formation and melanogenesis having the same action spectrum so proving that UV does induce melanogenesis. The CBDs stimulate melanogenesis by up-regulating and activating the p53 tumor suppressor system in keratinocytes, with the p53 acting as a transcription factor binding to the POMC promoter stimulating the formation of POMC which is selectively catabolised to form α-MSH, ACTH and endorphins. α-MSH binding to MC1-R also has the effect of activating the MITF system in a similar way to the cytokines as above. In addition, α-MSH also binds to receptors on the melanocyte surface such as MC1-R, which then activates adenylyl cyclase, and eventually MITF as described above resulting in activating the tyrosinase and other enzymes such as the tyrosinase-like proteins 1 and 2 that are essential for melanin formation. Another pathway by which UV stimulates melanogenesis is by it directly stimulating keratinocytes and fibroblasts in the skin, which produce Stem Cell Factor (SCF) in response, which then binds to its cKit receptor (cKitR) which induces mitogen activated protein kinases (MAPKs) that phosphorylate and thus activate MITF which activates the melanogenesis pathway as described above.

These processes involving MC1-R are known to be antagonised by agouti signalling peptides, which act as antagonists to the binding of α-MSH to the MC1-R, and has the effect of reducing melanin formation and of increasing the proportion of pheomelanins that are produced in the absence of α-MSH, and thus the modifying the skin tone of people to a more red tone.

Singlet oxygen stimulates keratinocytes and fibroblasts to produce cytokines, especially endothelin receptor type B-1 (ETB1), SCF and hepatocyte growth factor (HGF). These bind to receptors on the melanocytes with ETB1 and SCF binding to the receptors endothelin receptor type B-2 (ETB2) and cKitR respectively. Once activated these receptors stimulate the MITF system in the nucleus of the melanocytes, for instance the binding of SCF to its cKitR induces mitogen activated protein kinase which phosphorylates MITF thereby activating it. Activated MITF up-regulates the production of a number of proteins including tyrosinase, tyrosinase-like protein 1 (TLP1) and tyrosinase-like protein 2 (TLP2) that catalyse essential stages in the melanogenesis metabolic pathway, and melanophilin that is one of the proteins involved in the transfer of melanin in the form of melanosomes to keratinocytes, involving their binding to Rab27a and moving along the dendrites of the melanocytes via myosin filaments. In addition the formation of the prostaglandin PGE2 is stimulated by singlet oxygen, which in addition to causing inflammation also stimulates the production of matrix metalloproteases (MMPs) that play important roles in skin ageing due to their imperfect repair of damaged skin proteins over very many episodes of sun exposure, and also more specifically by degrading collagen IV in the basement membrane of the skin that leads to the formation of sun spots (senile lentigo).

While there are many cosmetic and personal-care products available in the market, the development of improved and efficient formulations in cosmetic and personal-care products for skin lightening, skin quality has and continue to receive significant public interest. Along with this has been the desire to establish cosmetic compositions that provide the features of good skin compatibility especially low irritancy potential, enhanced activity, reduced viscosity, enhanced antimicrobial activity without additional preservatives and prolonged shelf-life. In addition, these features and properties need to be provided in a safe, legal and cost-effective way.

Consequently, there is a need to provide alternative compositions and methods for regulating skin quality that seeks to address at least some of the problems described hereinabove, or at least to provide an alternative.

SUMMARY OF THE INVENTION

In accordance with one aspect of the invention, a cosmetic or personal care composition for regulating skin quality or skin lightening is provided. The composition comprises two or more compounds, each compound containing an allylic or partially allylic carbonyl substructure having the following structure I:

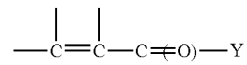

wherein Y is a second substructure immediately adjacent to the allylic or partially allylic carbonyl substructure and is selected from one of the following groups consisting of:
  (i) hydroxyl-based group including —OH or —C(=)—(OH);
  (ii) carbonyl-based group including —C(=)—C(=O)—CH$_3$;
  (iii) ether group, —O—;
  (iv) sultam group, —N(H)—S(=O)$_2$—;
  (v) lactam group, —N(H)—C(=O)—;
  (vi) apolar group including cyclic structures based on menthol or carotenoids;
  (vii) secondary aldimine containing group including —N(H)—C(NH$_2$)=N— or —N(H)—C(H)=N—;
  (viii) amine group, —NH$_2$;
  (ix) secondary amine-based group, —N(H)—; and
  (x) amide-based group including —N(H)—C(=O)— or —N(H)—C(=O)—N(H)—;
their derivatives, isomers, salts and/or combination thereof; and a cosmetically acceptable vehicle.

In accordance with embodiments of the invention, the two or more compounds are selected from one or more of the following groups:
  (a) gamma-pyrone compound and their salts thereof having the allylic or partially allylic carbonyl substructure immediately adjacent to the second substructure Y consisting of the hydroxyl or hydroxyl-based group;
  (b) gamma-pyrone compound and their salts thereof having the allylic or partially allylic carbonyl substructure immediately adjacent to the second substructure Y consisting of the carbonyl or carbonyl-based group;
  (c) sultam compound and their salts thereof containing the allylic or partially allylic carbonyl substructure immediately adjacent to the second substructure Y consisting of the sulphonamide group forming a sultam ring structure;
  (d) indole-like compound and their salts thereof composed of bicyclic aromatic and heterocyclic five membered rings containing the allylic carbonyl substructure immediately adjacent to the second substructure Y consisting of an amide group and forming a lactam structure;
  (e) cyclohex-2-enone-like compound and their salts thereof having the allylic or partially allylic carbonyl substructure immediately adjacent to the second substructure Y that contains a second unsaturated bond making the compound diallylic or partially diallylic;
  (f) adenine-like compound and their salts thereof with five and six-membered heterobicyclic structures containing the allylic or partially allylic carbonyl substructure adjacent to the second substructure Y consisting of one or more secondary aldimine groups and one or more secondary amine groups; and (g) purine-like or xanthine-like compound and their salts thereof containing the allylic or partially allylic carbonyl substructure immediately adjacent to the second substructure Y consisting of a secondary amine group or the —N(H)—C(=O)—N(H)— group.

In accordance with an embodiment of the invention, the two or more compounds each contain different Y substructure. In accordance with other embodiments of the invention, the two or more compounds each contain different Y substructure, with each of the Y substructures selected from different groups (i)-(x).

In accordance with yet other embodiments of the invention, the composition comprises two or more compounds containing the same or different Y substructures selected from the same or different groups (i)-(x), and one or more other skin lightening agents.

In accordance with an embodiment of the invention, the two or more compounds are selected from the group consisting of saccharin, maltol, theobromine, their derivatives, isomers, salts and combination thereof.

In accordance with another aspect of the invention, a method of regulating skin quality of a subject is provided. The method comprises the step of topically applying an effective amount of the cosmetic or personal care composition of the present invention on the skin of a subject.

In accordance with a further aspect of the invention, a method of skin lightening comprising the step of topically applying an effective amount of the cosmetic or personal care composition of the present invention on the skin of a subject, for lightening of skin is provided.

In accordance with yet another aspect of the invention, a method of determining a composition for use in regulating or improving skin quality of a subject is provided. The method comprises measuring skin quality of a subject; identifying two or more compounds with melanogenesis inhibiting activities by selecting two or more compounds, each compound containing an allylic or partially allylic carbonyl substructure having the following structure I:

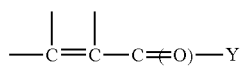

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—CH$_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$;
(ix) secondary amine-based group, —N(H)—; and
(x) amide-based group including —N(H)—C(=O)— or —N(H)—C(=O)—N(H)—; and preparing a formulation based on the measured skin quality so as to improve the skin quality using the identified compounds.

In accordance with yet a further aspect of the invention, a method of determining a composition for use as a skin lightening agent is provided. The method comprises determining the skin type of a subject; identifying two or more compounds with melanogenesis inhibiting activities by selecting two or more compounds, each compound containing an allylic or partially allylic carbonyl substructure having the following structure I:

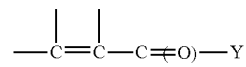

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—CH$_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$;
(ix) secondary amine-based group, —N(H)—; and
(x) amide-based group including —N(H)—C(=O)— or —N(H)—C(=O)—N(H)—; and preparing a formulation based on the determined skin type of the subject using the identified compounds.

In accordance with a further aspect of the invention, a method of identifying a compound with melanogenesis inhibiting activities is provided. The method comprises selecting a compound containing an allylic or partially allylic carbonyl substructure having the following structure I:

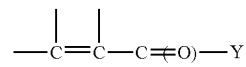

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—CH$_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$;
(ix) secondary amine-based group, —N(H)—; and (x) amide-based group including —N(H)—C(=O)— or —N(H)—C(=O)—N(H)—.

Other aspects of the invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention, in which.

DETAILED DESCRIPTION (A) Definitions

Figure 1:
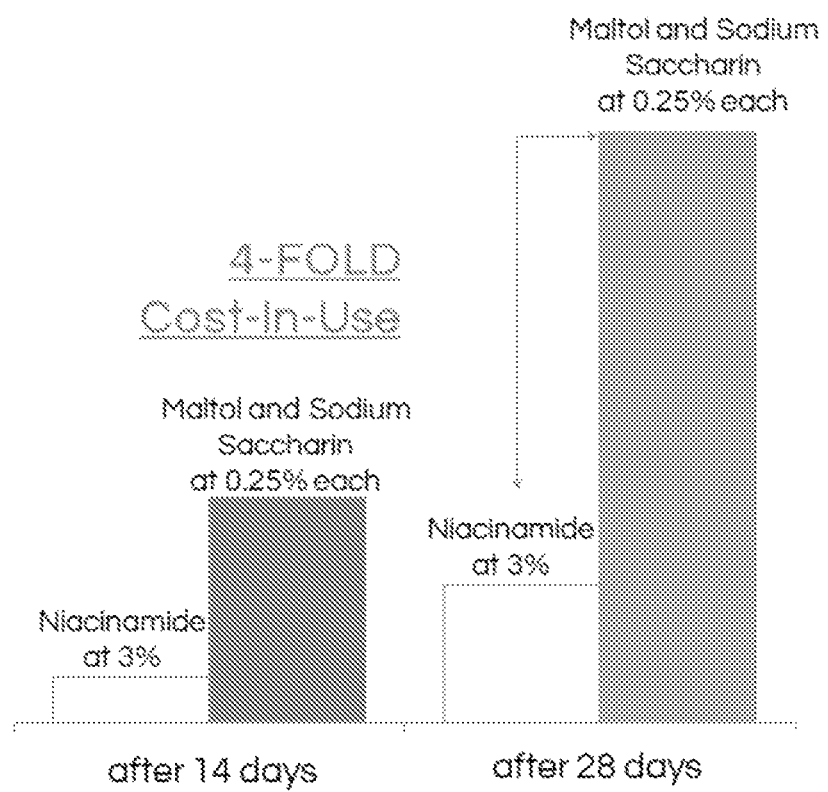
FIG. 1 is a chart showing the results obtained in a clinical trial. The chart shows the cost-in-use comparison between a product composition containing niacinamide and a product composition containing maltol and sodium saccharin.

Unless defined otherwise, all technical and scientific terms used herein have the same meaning as is commonly understood by a skilled person to which the subject matter herein belongs. As used herein, the following definitions are supplied in order to facilitate the understanding of the present invention.

As used in the specification, the singular form "a", "an" and "the" include plural references unless the context clearly dictates otherwise.

As used in the specification, the term "alkyl" refers to a saturated or unsaturated group comprising carbon and hydrogen atom.

As used in the specification, the prefix "cyclo" refers to structure in ring form.

Throughout this document, unless otherwise indicated to the contrary, the terms "comprising", "consisting of", and the like, are to be construed as non-exhaustive, or in other words, as meaning "including, but not limited to".

(B) Screening Method

Until comparatively recently customers just required products which were as effective as possible at lightening the skin. But now, new needs have arisen. It is no longer enough to just search for more effective skin lightener compounds or materials that produce a fairer skin or act more rapidly, but for compounds or materials that also give significant improvements to the radiant and youthful characteristics of skin, that also have excellent cosmetic benefits such as skin-feel and evenness of application. Other marketing-related advantages such as the use of natural or traditional sources of ingredients and an absence of synthetic preservatives are also desirable. In addition, these benefits and properties need to be provided in a convenient, stable, safe, legal and cost-effective way. The solution to the above needs is therefore not just a more active skin lightener that contains active ingredient such as a compound that inhibits tyrosinase more effectively, but an ingredient that satisfies customers' requirements which are commonly referred to as skin anti-ageing.

Skin ageing occurs as a natural consequence of ageing, the so called chronological ageing. This occurs as a result of exposure to sunlight and in particular, UVA radiation, which is referred to as photo-ageing. A common cause of these types of ageing is that they both occur cumulatively as a result of exposure to reactive oxygen species that possess one or more unpaired electrons. In chronological ageing, the ROSs are produced by metabolism, and in photo-ageing, by the action of UV photons. Visible signs of skin ageing include fine lines and wrinkles, pigmented spots such as 'age spots', and a general loss of elasticity and firmness of the skin. Physiologically, skin ageing is associated with degradation of the extracellular matrix and a flattening of the epidermal-dermal junction. Mechanisms of skin ageing include how UV light stimulates the production of cytokines that in turns stimulates the formation of matrix metalloproteinases such as elastase and collagenase. This degrades the extracellular matrix and damages the epidermal-dermal junction which can result in the formation of age spots.

In response to these multiple requirements, the following approach has been adopted, starting with the understanding that because of the many different physiological processes that contribute to skin appearance and skin ageing, many different active ingredients are required, and because melanogenesis is now known to be a complex process, both as regard the number of steps in the metabolic pathway involved and in the signalling pathways that control it. Therefore, in order to be very effective, a skin lightener needs to inhibit or antagonise as many as possible of the steps in the melanogenesis metabolic and signalling pathways, such as enzymes and receptors. To do this, a number of active ingredients are necessary, but ideally with each active ingredient having multiple different mechanisms of action so as to both inhibit as many of the steps in the melanogenesis metabolic and signalling pathways, as well as to enhance skin quality by lightening skin in a way that enhances the tone of the lightened skin and achieving other skin quality improvements such as improvement in skin smoothness and reduction in wrinkles and fine lines.

Consequentially, multifunctional compounds with a minimum of two or more of the skin lightening and skin quality improving activities, as well as with high specific activities were searched and identified. This is so as to reduce both the number of compounds that need to be co-formulated and the concentrations of active ingredients that have to be formulated so as to reduce the chance of undesirable effects, such as skin irritation, occurring on the skin. Complementary combinations of compounds with different structures and thus different activities were then devised, again to seek further skin quality benefits such as their contribution to fragrance and aroma, skin feel and ease of application of formulated products.

Variations on the combinations of high specific activity and multifunctional compounds can then be made to meet the specific requirements of particular groups of consumers, and ultimately the requirements of individual customers. The identified compounds can then be packaged or formulated into single or multi-use forms such as capsules or jars; and in different activities appropriate to customers who wish to enhance their skin quality rapidly or more quickly, and to maintain the desired skin quality achieved.

To obtain such multifunctional active ingredients, the compounds that were selected should have natural, traditional, safe, legal and cost-effective characteristics and properties that make the compounds acceptable and affordable to mass-market to customers and making it useable in high-street as well as luxury brands as well. The compounds were then screened for the possession of multiple mechanisms of action, which may be at one or more stages in the melanogenesis pathway itself and/or in the signalling pathways that control the synthesis and distribution of melanin, together with beneficial effects on skin quality factors such as radiance, skin tone, reduced wrinkles and age spots, anti-irritant properties, and improved softness, smoothness, evenness of tone and elasticity that contribute to a skin anti-ageing effect and a glowing and youthful appearance. Reduction of microbial growth on the skin is also desirable so as to reduce damage by UV light due to microorganisms depositing materials on the skin that accentuate the effects of UV radiation, such as porphyrins.

The screening method used in the present invention is aided by an understanding of the structural characteristics and/or substructures that are associated with, and that at least in part dictate, the mechanisms of action of the compounds they occur in, relatively independently of the complete chemical structures of the compounds. Any single structure or substructure may exert two or more different mechanisms of action. For instance, particular substructures tend to be responsible for one or more mechanisms of action that include the following general types: scavenging reactive oxygen species produced by the action of UV-light on the skin; acting as antagonists in the signalling pathways such as versus agonists, for example, α-MSH at MC1-R receptors; inhibiting enzymes such as tyrosinase or TLP1 and TLP2; or down-regulating the synthesis of proteins such as cytokines and enzymes involved in melanogenesis, especially via transcription factors such as MITF; and the packaging of melanin into the melanosomes and transfer to the keratinocytes. Advantages of this approach are that it selects active compounds that would not be detected in simple screens based on the inhibition of a single enzyme, or that do not allow UV-induced pathways to be tested.

The screening method further comprises screening for compounds with additional cosmetic benefits such as the abilities to give stable products that, when formulated, do not discolour the product, do not separate the product into different phases, do not become microbially contaminated, oxidised, or stain clothes. Other benefits include improving the physical stability of the formulation, reducing the viscosity of the formulation so that additional active ingredients can be added without reducing the ease of application and skin feel of the cosmetic product.

The uses of the identified compounds were then evaluated in combination for ability to achieve fast and effective skin lightening, and a high quality of lightened skin, achieved in a mild and gentle manner that is best carried out by only partially inhibiting several stages in the melanogenesis pathway and/or signalling pathways or other physiological processes, so that the overall cumulative effect on skin lightness and quality is greater than if any single active ingredient with a single mechanism of action is used. Whereas when a combination of different skin lightening active ingredients is used, they act rapidly to produce a high quality visibly lightened skin, together with other benefits as detailed hereinabove.

Using this approach in selecting suitable candidate for use in skin lightening and skin quality enhancement, a range of structurally diverse compounds having skin lightening, skin tone and skin quality improving and/or formulatory benefits has been identified. The compounds possess a number of different but complementary mechanisms of action.

Accordingly, in one aspect of the invention, a method of identifying a compound with melanogenesis inhibiting activities is provided. The method comprises selecting a compound containing an allylic or partially allylic carbonyl substructure having the following structure I:

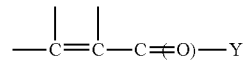

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—CH$_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$;
(ix) secondary amine-based group, —N(H)—; and
(x) amide-based group including —N(H)—C(=O)— or —N(H)—C(=O)—N(H)—;

It was found that efficacy of skin lightening and skin quality improvements can be maximized by using a combination of compounds, with each compound containing the allylic or partially allylic carbonyl substructure of structure I and a second substructure Y selected from one of the groups (i)-(x) as described hereinabove. It was found that the compounds work best when used in combination with each other, particularly when compounds with different substructure Y are combined, as each of the compounds with the different substructure Y would have different mechanisms of action and the compounds can therefore inhibit multiple melanogenesis pathways.

The substructures identified as determining the skin lightening activities of the compounds of the present invention are essential in identifying and designing composition with melanogenesis inhibiting activities. Without these substructures, costly, time- and effort-consuming high throughput screening would be required, while on the contrary, the substructures enable very productive low throughput screenings to be carried out.

The compounds of the present invention possess activities that improve skin tone and skin quality, and have formulatory advantages. The compounds can be used to advantage in combination with each other, and especially when formulated into cosmetic and personal care products in combination with complementary compounds and materials that potentiate their skin lightening activities, such as epidermal penetration enhancers, or reduce skin pigmentation such as UV absorbers, UV blockers and with currently used skin lighteners, and that have rejuvenating and anti-ageing activities and/or formulatory advantages such as shelf-life extending activities.

(C) Compounds and Composition

In accordance with an aspect of the invention, a cosmetic or personal care composition for regulating skin quality or skin lightening is provided. The composition comprises two or more compounds, each compound containing an allylic or partially allylic carbonyl substructure having the following structure I:

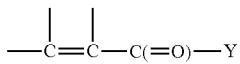

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—CH$_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$;
(ix) secondary amine-based group, —N(H)—; and
(x) amide-based group including —N(H)—C(=O)— or —N(H)—C(=O)—N(H)—;
their derivatives, isomers, salts and/or combination thereof; and a cosmetically acceptable vehicle.

The two or more compounds and/or their derivatives, isomers, salts and/or combination thereof that contain the allylic or partially allylic carbonyl substructure (ACSS) are selected from one or more of the following groups consisting of:
(a) Gamma-pyrone compounds and their salts thereof that contain the allylic or partially allylic carbonyl substructure immediately adjacent to the second substructure Y consisting of the hydroxyl or hydroxyl-based group. Compounds belonging to this group act by inhibiting tyrosinase, as antioxidants including as scavengers of reactive oxygen species such as singlet oxygen, and inhibiting the formation of cytokines. Examples of such compounds include, but are not limited to, maltol, ethyl maltol, acetyl salicylic acid, aconitic acid and protocatechuic acid;

(b) Gamma-pyrone compounds and their salts thereof that contain the allylic or partially allylic carbonyl substructure immediately adjacent to the second substructure Y consisting of the carbonyl or carbonyl-based group. Example of such compound includes, but is not limited to, dehydroacetic acid;

(c) Sultam compounds and their salts thereof that contain the allylic or partially allylic carbonyl substructure immediately adjacent to the second substructure Y consisting of the sulphonamide group forming a sultam ring structure. Compounds belonging to this group act as antagonists at the MC1-R receptor. Examples of such compounds include, but are not limited to, saccharin, sodium saccharin and potassium acesulphame;

(d) Indole-like compounds and their salts thereof composed of bicyclic aromatic and heterocyclic five membered rings containing the allylic carbonyl substructure immediately adjacent to the second substructure Y consisting of an amide group and forming a lactam structure. Compounds belonging to this group inhibits tyrosine-like protein 1 and/or 2. Example of such compound includes, but is not limited to phthalimide;

(e) Cyclohex-2-enone-like compounds and their salts thereof having the allylic or partially allylic carbonyl substructure immediately adjacent to the second substructure Y that contains a second unsaturated bond making the compound diallylic or partially diallylic. Compounds belonging to this group have mechanisms of action that include scavenging reactive oxygen species such as singlet oxygen and inhibiting the formation of cytokines. Example of such compounds includes, but is not limited to canthaxanthin;

(f) Adenine-like compounds and their salts thereof with five and six-membered heterobicyclic structures containing the allylic or partially allylic carbonyl substructure adjacent to the second substructure Y consisting of one or more secondary aldimine groups and one or more secondary amine groups. Compounds belonging to this group act by mechanisms that include inhibition of adenylyl cyclase. Examples of such compounds includes, but are not limited to, guanine, guanosine, guanosine monophosphate, inosine, inosine monosphosphate; and (g) Purine-like or xanthine-like compounds and their salts thereof containing the allylic or partially allylic carbonyl substructure immediately adjacent to the second substructure Y consisting of a secondary amine group or the N(H)—C(=O)—N(H)— group. Compounds belonging to this group are known to be antagonists of adenosine binding receptors. The compounds act by mechanisms that include via inhibition of adenylyl cyclase, or that may inhibit adenylyl cyclase and therefore act as indirect inhibitors of protein kinase by depriving them of cyclic AMP, or may complex with thymine dimers and prevent them from binding to their receptors. Examples of such compounds include, but are not limited to, theobromine, hypoxanthine, xanthine and uracil.

In some embodiments, the two or more compounds are selected from the group consisting of:

| Compound | Chemical Structure | Compound | Chemical Structure |
|---|---|---|---|
| Maltol | 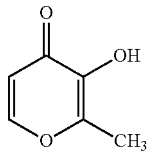 | Saccharin | 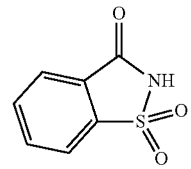 [SMILES: O=C1NS(=O)(=O)c2ccccc21] |
| Sodium Saccharin | 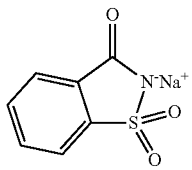 | Dehydroacetic Acid (DHAA) | 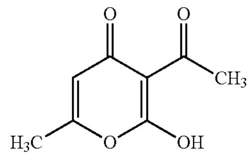 |
| Theobromine | 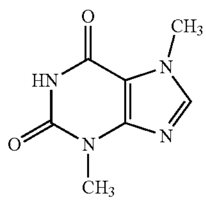 | Isodehydro-acetic acid | 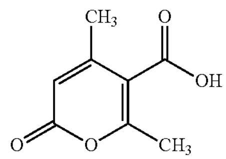 |
| Guanine | 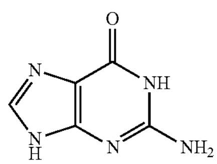 [SMILES: Nc1nc2[nH]cnc2c(=O)[nH]1] | Inosine | 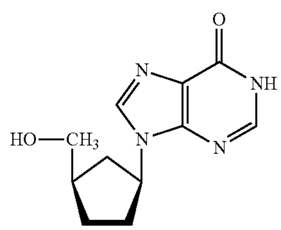 |
| Inosine Monophosphate (IMP) | | Hypoxanthine | |
| Ethyl Maltol | 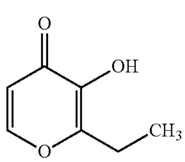 | Erythorbic Acid | 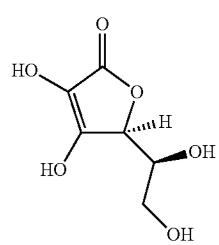 [SMILES: O=C1O[C@@H]([C@@H](O)CO)C(O)=C1O] |
| Citrazinic acid | 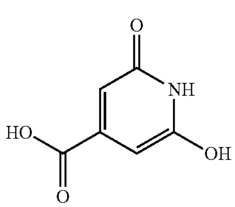 [SMILES: O=C(O)c1cc(O)[nH]c(=O)c1] | Isatoic Anhydride | 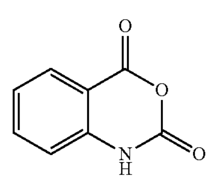 [SMILES: O=c1[nH]c2ccccc2c(=O)o1] |

-continued

| Compound | Chemical Structure | Compound | Chemical Structure |
| --- | --- | --- | --- |
| Protocate-chuic Acid (PCA) | | Nootkatone | |
| Cryptotan-shinone | | Acesulphame K (Potassium Acesulphame) | |
| S-carvone | 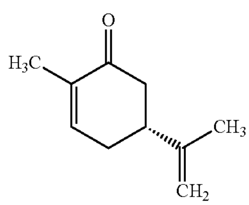 | R-carvone | 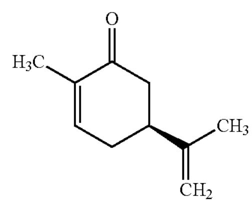 |
| Anthranil-amide | | Beta-damascenone | |
| Xanthine | 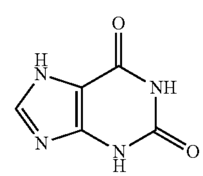 [SMILES: O=c1[nH]c(=O)c2[nH]cnc2[nH]1] | Methyl-anthranilate | 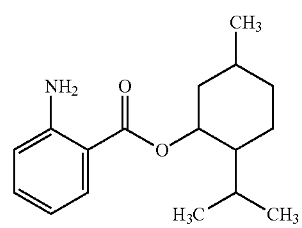 [SMILES: CC1CCC(C(C)C)C(OC(=O)c2ccccc2N)C1] |
| Trans-Aconitic Acid | 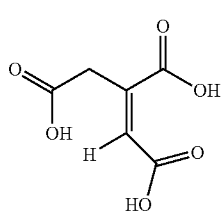 [SMILES: O=C(O)/C=C(/CC(=O)O)C(=O)O] | Cis-Aconitic Acid | 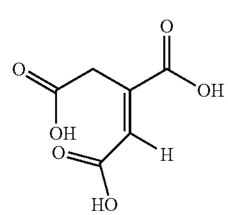 [SMILES: O=C(O)/C=C(\CC(=O)O)C(=O)O] |
| Phthalimide | 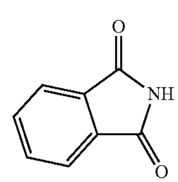 [SMILES: O=C1NC(=O)c2ccccc21] | 4-ketoiso-phorone | 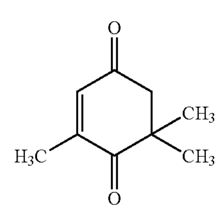 |

-continued

| Compound | Chemical Structure | Compound | Chemical Structure |
| --- | --- | --- | --- |
| Uracil | 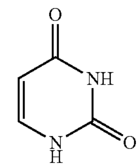 | Guanosine | 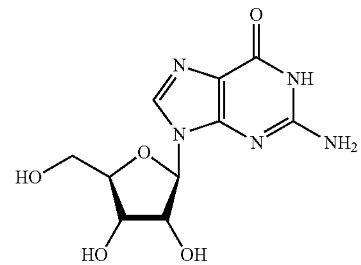 |
| Rosmarinic Acid | 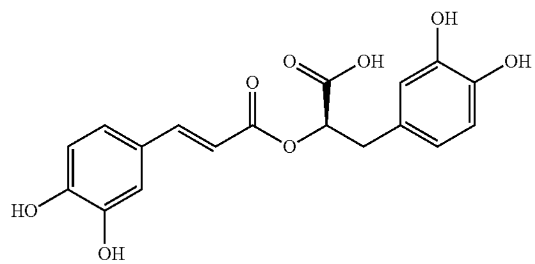 [SMILES: O=C(/C=C/c1ccc(O)c(O)c1)O[C@H](Cc1ccc(O)c(O)c1)C(=O)O] | | |
| Guanosine Monophosphate | | | |
| Canthaxanthine | | | |
| Isoamyl Cinnamate | 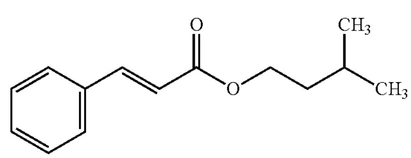 [SMILES: CC(C)CCOC(=O)/C=C/c1ccccc1] | | |
| Acetyl Salicylic Acid | | | | and their derivatives, isomers, salts and/or combination thereof.

The compounds of the present invention may be provided in the form of an extract derived from a plant material or yeast. Examples of such compounds include, but are not limited to, maltol, theobromine, hop extracts and yeast extracts containing inosine, guanosine monophosphates and/or purines.

In some embodiments, the two or more compounds each contain different Y substructures. In other embodiments, the two or more compounds each contain different Y substructures, with each of the Y substructures selected from different groups (i)-(x).

In further embodiments of the invention, the composition comprises two or more compounds containing the same or different Y substructure, with each of the Y substructures selected from the same or different groups (i)-(x), and one or more other skin lightening agents.

The compounds as described hereinabove include compounds in which UV-induced melanogenesis is reduced by some combination of inactivating initiators of melanogenesis signalling pathways produced by the action of sunlight such as UV radiation and in particular UVB radiation on the skin, by inhibiting one or more of the stages in a melanogenesis pathway or one or more melanogenesis signalling pathways, and by inhibiting one or more stages in the melanogenesis pathway from precursor amino acid to melanin transferred into keratinocytes.

The compounds as described hereinabove include compounds that possess some combination of melanogenesis inhibiting, skin tone improving, enhancing effects on one or more aspects of skin quality such as enhancing the smoothness of skin or reducing wrinkles or dark circles around the eyes, and one or more formulatory benefits such as extending the shelf-life of cosmetic products by preventing the growth of microbial contaminants.

The two or more compounds of the present invention may possess different combination of two or more different skin quality improving activities and with different useful mechanisms of action because of the complexity of the melanogenesis process and the range of desirable skin quality effects and properties. The desirable skin quality effects and properties include skin lightening, improving the skin tone and other desirable skin features such as smoothness, reducing wrinkles and dark circles around the eyes, and formulatory advantages for the cosmetic products they are used in such as to extend the shelf-lives or by reducing the viscosity of the creams and so improve their ease of spreading on the skin so that each compound has different multifunctional skin quality improving properties.

The composition of the present invention comprising the two or more compounds as described hereinabove has two or more skin lightening and skin quality improving effects such as by improving the skin tone by increasing a* (rosy-red tone) and/or reducing b* (yellow skin tone) components respectively, and/or by reducing fine lines and wrinkles, the intensity of pigmented spots or microbial damage; and/or improving skin radiance, anti-irritant properties, softness, smoothness, elasticity, skin cell regeneration and evenness of appearance, and other characteristics of youthful skin. The effects are proven and illustrated in Examples 5, 6 and 7 below.

The composition of the present invention comprising the two or more compounds as described hereinabove possess one or more characteristics or properties that give quality benefits in the form of formulatory advantages when the compounds are used in cosmetic or personal care products. The composition possess shelf-life extending properties, a positive aroma, a reduced viscosity of creams on the products the composition is added to and so improve the ease of spreading of the creams on the skin, or resistance to colour formation on storage. These characteristics or properties are illustrated in Examples 8, 9 and 10 below.

The composition of the present invention has high specific activities such that the composition can produce visibly improved skin within just one to two weeks of use even when used at low concentrations and without any additional ingredients to improve the activities such as epidermal penetration enhancers, and to improve the consumer products they are used in, such as being able to make preservative-free claims, thereby minimising any skin irritancy due to chemicals preservatives used or other undesirable effects. These characteristics or properties are illustrated in Example 1 and 17.

The composition of the present invention can visibly reduce the degree of pigmentation of human skin within 14 days when applied twice daily dissolved in a cream or some other similar form at a dose of less than 1% w/w but without any other active materials such as penetration enhancer ingredients being present in the cream that can enhance the activity of the compounds, or that can reduce UV-induced skin pigmentation such as UV-absorbers, that are generally less available and so more expensive than the compounds of this invention so that easy to formulate and low cost end-products can be made. This effect is illustrated in Example 1 below.

In some embodiments, the composition of the present invention includes compounds with skin lightening activities that reduce endogenous and/or UV-induced melanogenesis, together with some combination of additional skin tone, skin quality improving, and/or cosmetic and formulatory advantages. An exemplary embodiment of this invention includes a composition comprising two or more compounds selected from the group consisting of saccharin, maltol, theobromine, their derivatives, isomers, salts and/or combination thereof. In one embodiment, the composition comprises saccharin and/or its salts thereof and maltol, preferably sodium saccharin and maltol. In another embodiment, the composition comprises maltol and theobromine. In yet another embodiment, the composition comprises saccharin and/or its salts thereof, maltol and theobromine.

Maltol has also been proven to be an in-vivo skin lightener, and with an ex-vivo melanogenesis reducing activity, together with antioxidant activity, skin tone and skin quality improving activities.

In Example 3 below, it is shown that maltol (3-hydroxy-2-methyl-4H-pyran-4-one) can effectively reduce melanogenesis activity as a result of testing the lightening effect of maltol on cultured melanocytes (see Table X in Example 3) with an IC50 of 0.065 g/l in B16 cultured melanocyte assays The composition comprising maltol has no significant tendency to decolourise when formulated in a concentration of less than 2% into cosmetic or personal care products. The composition possesses antimicrobial and antioxidant activities sufficient to extend the shelf-lives of the formulated cosmetic or personal care products without the need for any other preservative ingredients. The activities of maltol as described hereinabove are described in Tables I, II, III, V, VI and X, and Examples 1 and 3 below.

Sodium saccharin has been proven to have skin tone and skin quality improving activities including skin radiance-brightness imparting properties, together with viscosity reducing properties when formulated into products, antimicrobial activity sufficient to extend the shelf-lives of formulated products without the need for any other preservative ingredients, and ability to form zinc saccharide when saccharin is formulated with a source of zinc such as zinc hydroxide or oxides, together with in-vivo skin lightener activity, with an ex-vivo melanogenesis reducing activity of IC50 of 0.055 g/l in B16 cultured melanocyte assays (see Table X and Example 3). The activities of sodium saccharin as described hereinabove are described in Tables I, II, III, V, VI, X, and Examples 1, 3 and 16 below.

Sodium saccharin when used in combination with maltol, forms a cosmetic composition that yields better antimicrobial activity based on the weight of the composition as opposed to sodium saccharin or maltol being used individually, thereby the combination extends the shelf-life of the formulated cosmetic or personal care product. In Example 3 below, it is shown that sodium saccharin when used in combination with maltol can effectively reduce melanogenesis activity as a result of testing the lightening effect of the combination on cultured melanocytes (see Table X in Example 3). with an IC50 of 0.046 g/l in B16 cultured melanocyte assays, lower than if maltol or sodium saccharin were to be used on its own. The activities of sodium saccharin when used in combination with maltol as described hereinabove are described in the relevant Tables and Examples below.

Both maltol and saccharin (and sodium saccharin) have good antimicrobial activities, but when used in B16 assays or on human skin (in clinical studies), both are exposed to mammalian cells that one would expect to be more sensitive than microbial cells. However, the mammalian cells are hardly affected. Both maltol and saccharin or the combination of maltol and saccharin show no real cytotoxic activities on ether the B16 cells or on intact human skin.

As regards its melanogenesis inhibiting activities, maltol is a tyrosinase inhibitor and also an antioxidant, including scavenging the singlet oxygen generated by the action of sunlight on skin. By contrast, saccharin (2H-1lamda 6, 2-benzothiazol-1,1,3-trione) does not have either tyrosinase inhibiting or antioxidant activities; but it contains a lipophilic group in the form of its aromatic ring combined with its amide and sulphonamide groups giving it an analogous structure to the 'pharmacophore' of Agouti signalling peptides (ASPs) that contains a phenylalanine and its associated amide bonds. Since ASPs have been identified as endogenous antagonists of $\alpha$-MSH binding to MC1-R, and so act as a physiological inhibitor of melanin synthesis, it is likely that saccharin has a similar antagonist and melanogenesis inhibiting activities, particularly as combinations of its lipophilic and both its amide or its sulphonamide groups, could mimic the antagonist activity of the ASP pharmacophore. The complementary skin quality enhancing activities of maltol and saccharin can be similarly explained. Singlet oxygen stimulates cytokines that activate not just melanogenesis, but also the formation of MMPs, such as collagenases and elastases that play key roles in skin ageing and in age spot formation. Likewise the antagonism of $\alpha$-MSH binding to MC1-R not only inhibits melanogenesis but also increases the proportion of pheomelanins produced, rather than eumelanins, giving the skin a rosier and more youthful appearance.

The use of active compounds with different but complementary mechanisms of action and characteristics extends to the formulatory benefits of combinations of the compounds of the present invention. While maltol has bactericidal activity, saccharin is bacteriostatic interfering with folic acid synthesis. Saccharin and maltol have different water solubility, and therefore they tend to protect different phases of emulsified products and have different epidermal penetration properties. It has been shown that the use of sodium saccharin or saccharin in conjunction with maltol significantly reduces the viscosity of the cosmetic and personal care products. This is advantageous as a reduced viscosity allows for the addition of other compounds (for example, potassium acesulphame including particulates such as titanium dioxide or zinc oxide), thus providing more flexibility to formulators, without reducing the ease of application and skin feel of the product. Furthermore, sodium saccharin used in combination with maltol also provides a more pleasant fragrance, as opposed to either active ingredient being used individually.

In various embodiments, the two or more compounds present in the cosmetic or personal care composition include maltol in an amount ranging from 0.01 to 10 wt % based on the total weight of the composition. In other embodiments, maltol is present in an amount of 0.02 to 5 wt % based on the total weight of the composition. In further embodiments, maltol is present in an amount of 0.01 to 1 wt % or about 0.25 wt % based on the total weight of the composition.

In various embodiments, the two or more compounds present in the cosmetic or personal care composition include saccharin and/or its derivative, including its cosmetically acceptable salt such as sodium saccharin. In various embodiments, saccharin or sodium saccharin is present in an amount ranging from 0.01 to 70 wt % based on the total weight of the composition. In other embodiments, saccharin or sodium saccharin is present in an amount of 0.01 to 60 wt % based on the total weight of the composition. In other embodiments, saccharin or sodium saccharin is present in an amount of 0.01 to 50 wt % based on the total weight of the composition. In yet other embodiments, saccharin or sodium saccharin is present in an amount of 0.01 to 40 wt % based on the total weight of the composition. In further embodiments, saccharin or sodium saccharin is present in the composition in an amount 0.01 to 30 wt % based on the total weight of the composition. In further embodiments, saccharin or sodium saccharin is present in the composition in an amount of 0.01 to 20 wt % based on the total weight of the composition. In yet further embodiments, saccharin or sodium saccharin is present in the composition in an amount of 0.01 to 10 wt % based on the total weight of the composition. In yet further embodiments, saccharin or sodium saccharin is present in an amount of 0.02 to 5 wt % based on the total weight of the composition. In various embodiments, saccharin or sodium saccharin is present in the composition in an amount of 0.01 to 1 wt % or about 0.25 wt % based on the total weight of the composition.

Theobromine has a melanogenesis reducing activity of IC50 of 0.037 g/l in B16 cultured melanocyte assays, as described in Table X and Example 3. It can also be used in the form of cocoa extracts.

Other compounds with similar structures to maltol include ethyl maltol, acetyl salicylic acid, citrazinic acid and dehydroacetic acid. The IC50 values of these compounds range from of 0.059 to 0.262 g/l in B16 cultured melanocyte cell melanogenesis inhibition assays (see Table VI, Example 2). These compounds also tend to have bactericidal and fungicidal activities, and so can extend the shelf-life of the formulated products containing the said compounds. Further compounds include canthaxanthin, aconitic acid, protocatechuic acid, cryptotanshinone, ubiquinone, ubisemiquinone, the alpha-acids humulone, cohumulone and adhumulone, the beta-acids lupulone, colupulone and adlupulone, and hop extracts containing them, including boiled extracts containing isohumulone, humulinic acid and isohumulinic acid, and which can also contain xanthohumol and which is an inhibitor of the MMPs elastase and collagenase.

In one embodiment, the composition comprises a combination of compounds including saccharin, maltol, theobromine, potassium acesulphame and dehydroacetic acid.

Cyclic sulphamides/oxathiazolinone dioxides such as acesulphame and its salts, in particular, potassium acesulphame has a melanogenesis inhibiting activity with an IC50 of 0.058 g/l in B16 cultured melanocyte assays, as shown in Table X and Example 3 below.

The compounds of the present also include phthalimide and its salts, particularly, potassium phthalate that has indole-like structures. In particular, phthalimide has a melanogenesis inhibiting activity with an IC50 of 0.089 g/l in B16 cultured melanocyte assays, as shown in Table X and Example 3 below.

The compounds with similar purine structures include hypoxanthine (IC50 of 0.07 g/l, Table X, Example 3), xanthine, purine nucleosides and nucleotide derivatives such as Inosine monophosphate (IMP) (IC50 of 0.227 g/l, Table X, Example 3) and guanosine monophosphate (GMP) (IC50 of 0.07 g/l, Table X, Example 3) and their metabolites such as guanine (IC50 of 0.056 g/l, Table X, Example 3), hypoxanthine and xanthine, which can also be used in the form of yeast extracts. Also, compounds with similar substructures include citrazinic acid (IC50 of 0.077 g/l, Table X, Example 3) and isatoic anhydride (IC50 of 0.132 g/l, Table X, Example 3), and its hydrated product anthranilic acid N-carboxylic acid.

The skin quality enhancing activities of the compounds of the present invention can also be enhanced by their use as salts with cations with proven topical health and quality benefits such as zinc and copper in the form of homo-dimeric or hetero-dimeric salts. Examples of the homo-dimeric and hetero-dimeric zinc salts of the compounds of the present invention, in particular, maltol, dehydroacetic acid, saccharin, theobromine and acesulphame, include the homo-dimers $Zn(saccharin)_2$, $Zn(maltol)_2$, $Zn(theobromine)_2$, $Zn(dehydroacetic\ acid)_2$, $Zn(acesulphame)_2$; and the hetero-dimers saccharin-Zn-maltol, saccharin-Zn-acesulphame, saccharin-Zn-dehydroacetic acid, saccharin-Zn-theobromine; maltol-Zn-dehydroacetic acid, maltol-Zn-theobromine, maltol-Zn-acesulphame; dehydrocetic acid-Zn-theobromine, dehydroacetic acid-Zn-acesulphame and theobromine-Zn-acesulphame. The zinc salts are obtained when the said compounds are formulated with zinc compounds such as zinc oxide, zinc hydroxide or zinc gluconate so that their zinc salts are formed once the compounds are formulated (see Example 16).

Homo-dimeric and hetero-dimeric copper salts of the compounds of the present invention, in particular, maltol, dehydroacetic acid, saccharin, theobromine and acesulphame, include the homo-dimers $Cu(saccharin)_2$, $Cu(maltol)_2$, $Cu(theobromine)_2$, $Cu(dehydroacetic\ acid)_2$, $Cu(acesulphame)_2$; and the hetero-dimers saccharin-Cu-maltol, saccharin-Cu-acesulphame, saccharin-Cu-dehydroacetic acid, saccharin-Cu-theobromine; maltol-Cu-dehydroacetic acid, maltol-Cu-theobromine, maltol-Cu-acesulphame; dehydrocetic acid-Cu-theobromine, dehydroacetic acid-Cu-acesulphame and theobromine-Cu-acesulphame.

The compounds of the present invention include combinations of the above zinc and copper salts of the compounds of the present invention, and also the hetero-dimeric salts composed of one anion selected from the compounds described herein, for example, saccharin and a second anion selected from compounds known to have skin lightening and/or skin quality improving activities such as kojic acid to form hetero-dimeric salts such as saccharin-Zn/Cu-kojic acid, zinc/copper hetero-dimers that consist of one anion such as saccharin or maltol, etc, and a second anion that is a known anti-ageing or skin quality improving active such as ascorbic acid, or alpha-hydroxy acids, such as glycolic and lactic acids with desquamation activity, and zinc/copper hetero-dimers consisting of one anion that is a known skin lightening active as above together with a second anion that is a known anti-ageing active ingredient. In various embodiments, the salt comprises homo-dimeric and/or hetero-dimeric salts in which a zinc cation bridges the two identical or different anions. In other embodiments, the salt comprises homo-dimeric and/or hetero-dimeric salts in which a copper cation bridges the two identical or different anions.

The compounds of the present invention further include compounds in which their skin lightening mechanism or mechanisms of action include one or more of inactivating the products of UV damage to the skin that initiate melanogenesis such as reactive oxygen species, or the generation of cytokines and other signalling compounds, acting as antagonists or reverse agonists in the signalling pathways, inhibiting enzymes, affecting the activity of transcription factors, or by down-regulating the synthesis of proteins involved in melanogenesis.

The compounds of the present invention further include compounds that possess a structure or a substructure or substructures, that give them a mechanism or mechanisms of action for skin lightening, involving inhibition of the melanogenesis metabolic pathway and/or inhibition of one or more melanogenesis signalling pathways, and in addition, one or more mechanisms of action for improving the quality of skin tone and/or skin quality by inhibiting undesirable processes and/or by stimulating desirable processes, and involving one or more formulatory benefits.

The compounds of the present invention further include compounds that act as antagonists or reverse agonists at the MC1-R receptor and in doing so, inhibiting melanogenesis and modifying the colour of the melanins produced. This in turns modifies the skin tone to a more pink-red tone, thus showing how a single mechanism of action can produce quite distinct improvements in skin lightness and skin quality.

The compounds of the present invention include compounds that reduce the formation of cytokines known to stimulate the formation of fine lines and wrinkles, age spots and inflammation by reducing UV-induced MMP formation thus improving the quality of skin as well as inhibiting melanogenesis, again showing how a single mechanism of action can produce two distinct improvements in skin lightness and skin quality.

The compounds of the present invention include compounds that inactivate reactive oxygen species, such as singlet oxygen, and so inhibit the skin ageing effects; such as by antagonising the singlet oxygen stimulated production of cytokines and so reducing prostaglandin-stimulated inflammation and irritancy, matrix metalloproteinase formation, and thus wrinkle formation and the development of age spots for instance via preventing collagen 4 catabolism.

The compounds of the present invention include compounds that antagonise or inactivate thymine dimer photo-degradation products and so reduce their initiation of melanogenesis.

(D) Cosmetic Composition

In various embodiments, the cosmetic or personal care composition of the present invention comprises complementary combinations of two or more compounds, all of the compounds possess the common allylic or partially allylic carbonyl substructure (ACSS) of structure I. The combination of compounds possesses skin lightening activities together with one or more of skin tone improving, skin quality enhancing, and formulatory advantages, and with different physicochemical characteristics. With each of the compounds containing the common allylic or partially allylic carbonyl substructure of structure I, together with the different second substructure Y, the compounds possess different mechanisms of action. This enables each combination of two or more compounds to inhibit multiple different steps in melanogenesis, thus maximising their efficacy and the range of beneficial effects achieved as compared to using just one compound. The combination enables good effects even when the compounds are used in low concentrations and without requiring the use of any additional ingredients to improve the effects of the composition, thereby minimising any undesirable effects. Example 15 below illustrates these effects.

In various embodiments, the cosmetic or personal care composition for use in regulating skin quality comprises complementary combinations of two or more compounds of the present invention, in which the physicochemical characteristics include, but are not limited to, solubilities and log P values; the multiple different steps of melanogenesis including, but are not limited to, the inhibition of the melanogenesis metabolic pathway, inhibition of the compounds that initiate melanogenesis, inhibition of the various stages in the melanogenesis signalling pathways such as the formation of cytokines, antagonism of different steps in the melanogenesis signalling pathway, modification of the activity of transcription factors, and down-regulation of the formation of proteins or enzymes that participate in the melanogenesis metabolic or signalling pathways including shared mechanisms of action such as via the transcription factor MITF. The physicochemical characteristics further include not requiring any additional ingredients such as epidermal penetration enhancer compounds, materials and preservative chemicals to be added. This eliminates the undesirable effects which the additional ingredients may cause to the skin, including skin irritancy and sensitisation. Example 15 below illustrates these effects.

In some embodiments, the cosmetic or personal care composition of the present invention comprises two or more compounds selected from one of the combinations of the compounds consisting of maltol and/or dehydroacetic acid with saccharin, sodium saccharin, zinc saccharides or copper saccharides and/or potassium acesulphame and/or theobromine. In one embodiment, the composition comprises a combination of maltol and sodium saccharin. In this embodiment, the skin lightening, skin tone and quality improving, aroma, and shelf-life extending activities are enhanced by their different but complementary individual activities in formulations. For instance, saccharin is used in combination with maltol because both possess different but complementary inhibition of melanogenesis, skin tone and quality improving properties, and different formulatory characteristics such as the different antimicrobial activities and different solubility properties of maltol and sodium saccharin which give a more effective effect (see the Examples below).

In some embodiments, the cosmetic or personal care composition comprises a combination of zinc and copper salts of the compounds as described hereinabove. The salts include homo-dimeric and hetero-dimeric zinc salts of the compounds of the present invention including salts of maltol, dehydroacetic acid, saccharin, theobromine and acesulphame. Examples of such salts include, but are not limited to, the homodimers $Zn(saccharin)_2$, $Zn(maltol)_2$, $Zn(theobromine)_2$, $Zn(dehydroacetic\ acid)_2$, $Zn(acesulphame)_2$; and the heterodimers saccharin-Zn-maltol, saccharin-Zn-acesulphame, saccharin-Zn-dehydroacetic acid, saccharin-Zn-theobromine; maltol-Zn-dehydroacetic acid, maltol-Zn-theobromine, maltol-Zn-acesulphame; dehydrocetic acid-Zn-theobromine, dehydroacetic acid-Zn-acesulphame and theobromine-Zn-acesulphame, and combinations of the corresponding copper salts of the compounds of the present invention.

In some embodiments, the cosmetic or personal care composition comprises two or more compounds which are specifically combined for particular requirements of customers with different skin types, of different ages or ethnicities, or with other individual or group topical requirements. This is done by selecting combinations of compounds that act only, or predominantly, on just those enzymes, proteins, transcription factors, etc. whose activities need to be modified to meet the specific requirements of particular groups of people or individuals (see Example 5). Exemplary embodiments of variations of formulations are shown in Examples 14 and 15.

(E) Uses

In one embodiment, the present invention relates to the use of the two or more compounds of the present invention to formulate a cosmetic or personal care composition for regulating skin quality. The regulating of skin quality includes reducing endogenous and/or UV-induced melanogenesis; reducing activities of melanogenesis metabolic pathway and/or one or more of the signalling pathways that control the activity of the melanogenesis metabolic pathway; reducing the melanin content of the skin of a subject; lightening of the skin, pigmented spots, freckles, blemishes and dark circles around the eyes of the subject. The use further comprises enhancing skin quality activities including improving the tone and smoothness of lightened skin of the subject by increasing a* (rosy-red tone) and/or reducing b* (yellow skin tone) components, reducing fine lines and wrinkles of the subject by improving skin radiance, anti-irritant properties, softness, smoothness, elasticity, and evenness of appearance of the skin.

In another embodiment, the present invention relates to the use of a cosmetic or personal care composition as described hereinabove as a skin lightening agent.

In one embodiment, the use of the compounds as described hereinabove and the combinations thereof includes combinations of homo-dimeric and hetero-dimeric zinc salts of the compounds, in particular, maltol, dehydroacetic acid, saccharin, theobromine and acesulphame. Examples of such salts include, but are not limited to, homo-dimers $Zn(saccharin)_2$, $Zn(maltol)_2$, $Zn(theobromine)_2$, $Zn(dehydroacetic\ acid)_2$, $Zn(acesulphame)_2$; and the hetero-dimers saccharin-Zn-maltol, saccharin-Zn-acesulphame, saccharin-Zn-dehydroacetic acid, saccharin-Zn-theobromine; maltol-Zn-dehydroacetic acid, maltol-Zn-theobromine, maltol-Zn-acesulphame; dehydrocetic acid-Zn-theobromine, dehydroacetic acid-Zn-acesulphame and theobromine-Zn-acesulphame. The use also includes the use of the corresponding copper salts of the compounds as described hereinabove and combinations of the zinc and copper salts of the said compounds. Homo-dimeric and hetero-dimeric zinc/copper salts lighten and improve the tone and quality of skin, including possible effects against blemishes, such as reducing acne, and to achieve formulatory advantages such as shelf-life extension of products. These effects are illustrated in (Example 11, Example 16).

In some embodiments, the present invention relates to a cosmetic or personal care composition comprising a combination of two or more compounds, each of the compounds containing the allylic or partially allylic carbonyl substructure of structure I as described hereinabove, in combination with other compounds and materials that enhance the activity of the said two or more compounds, such as with other compounds and materials that prevent UV light from stimulating melanogenesis, for use in regulating skin quality or skin lightening. In some embodiments, the combination of the two or more compounds is selected from the group consisting of maltol and saccharin; maltol and sodium saccharin; maltol and zinc saccharide; and maltol and copper saccharide.

In some embodiments, the present invention relates to a cosmetic or personal care composition comprising a combination of two or more compounds, each of the compounds containing the allylic or partially allylic carbonyl substructure of structure I as described hereinabove, in combination with other compounds, plant extract and materials that also have melanogenesis inhibiting activities for use in regulating skin quality or skin lightening. In some embodiments, the combination of the two or more compounds is selected from the group consisting of maltol and saccharin; maltol and sodium saccharin; maltol and zinc saccharide; and maltol and copper saccharide. Examples of the plant extract and materials include, but are not limited to, niacinamide, licorice root extract, bearberry extract, alpha- and beta-arbutins, and ascorbic acid and its derivatives such as ascorbyl-2 glucoside and magnesium ascorbyl phosphate (see Example 1, Example 7, Example 12).

In further embodiments, the present invention relates to a cosmetic or personal care composition comprising a combination of two or more compounds, each of the compounds containing the allylic or partially allylic carbonyl substructure of structure I as described hereinabove, in combination with other compounds and materials that prevent UV light from stimulating melanogenesis (Example 12), for use in regulating skin quality or skin lightening. Such other compounds and materials include ultraviolet B absorbers (such as octyl methoxycinnamate) and/or ultraviolet A absorbers (such as butyl methoxy dibenzoylmethane) and/or UV blocking materials such as titanium dioxide and zinc oxide, antioxidants such as tocopherol, tocopherol acetate, ascorbic acid or ascorbyl palmitate, and ascorbic acid and its derivatives. In some embodiments, the combination of the two or more compounds is selected from the group consisting of maltol and saccharin; maltol and sodium saccharin; maltol and zinc saccharide; and maltol and copper saccharide.

In some embodiments, the present invention relates to a cosmetic or personal care composition comprising a combination of two or more compounds, each of the compounds containing the allylic or partially allylic carbonyl substructure of structure I as described hereinabove, in combination with other compounds with skin rejuvenating and anti-ageing activities (Examples 11 and 13), for use in regulating skin quality or skin lightening. Such other compounds include, but are not limited to, UV absorbing and blocking compounds and materials; antioxidants; inhibitors of collagenase and elastase; moisturisers such as glycerol, hyaluronic acid and its salts; phytosphingosine and ceramides; niacinamide that has anti-acne and ceramide stimulating activities; alpha-hydroxy acids such as lactic, citric and glycolic acids that have desquamation activity; anti-glycation agents such as garcinol, arginine and pyrrolidone carboxylic acid; anti-wrinkling active ingredients such as retinol and retinyl palmitate; and the UV absorbers and blockers; and antioxidants as described above. The composition comprising said compounds gives lightened skin younger, less aged characteristics such a smoother, softer feel and glowing appearance (Example 14).

In some embodiments, the present invention relates to a cosmetic or personal care composition comprising a combination of two or more compounds, each of the compounds containing the allylic or partially allylic carbonyl substructure of structure I as described hereinabove, in combination with other compounds and/or materials with formulatory characteristics complementary to their use, such as with shelf-life extending properties (Example 8).

In other embodiments, the present invention relates to a cosmetic or personal care composition comprising a combination of two or more compounds, each of the compounds containing the allylic or partially allylic carbonyl substructure of structure I as described hereinabove, in combination with other compounds for use in producing melanins of different tones and thus producing desirable skin tones in the lightened skin or maintaining the tone of lightened skin. Example of such compounds includes, but not limited to, self-tanning agents such as dihydroxyacetone.

In some embodiments, the present invention relates to a cosmetic or personal care composition comprising a combination of two or more compounds, each of the compounds containing the allylic or partially allylic carbonyl substructure of structure I as described hereinabove, in combination with another compound or compounds that are metabolised by the melanogenesis metabolic pathway to produce melanins of different tones and thus produce desirable skin tones in the lightened skin or maintain the tone of lightened skin.

In some embodiments, the present invention relates to the use of the compounds and combinations of the compounds of the present invention as described hereinabove, in cosmetic and personal care product formulations, such as skin lightener creams, lotions, moisturisers, facial mists, body sprays, sunscreen products, spot and blemish creams, eye creams, emulsions, serums, pressed serums, pastes, applicator sticks, essences, ointments, aerosols, sprays, mists, roll-ons, balms, gels, face masks, facial foams, toners, concentrates, ampoules, capsules, cosmetic waters, cosmetic compacts and foundations, soaps and body washes or in products with rejuvenating, anti-ageing or skin quality improving properties (for instance, see Examples 11, 12, 13 and 14), in particular, at concentrations of up to 10%, to provide a range of benefits, and using combinations of the compounds in different absolute and relative concentrations, in particular to provide a range of products with different activities to meet the specific requirements of different groups and individuals.

In one embodiment, the present invention relates to the use of compounds and combinations of compounds of the present invention as described hereinabove, in edible forms, for cosmetic and personal care purposes, such as, edible supplements, edible food and beverages, edible cosmeceuticals, nutraceuticals, edible tablets and edible vitamins.

In some embodiments, the present invention relates to a range of cosmetic formulations with complementary skin lightening, skin tone and quality improving effects and formulatory advantages, and with each formulation containing different combinations and absolute and relative concentrations of the compounds of the present invention as described hereinabove, such that each cosmetic formulations in the range provides a different combination of skin lightening, skin tone and skin quality activities and benefits.

In some embodiments, the present invention relates to the use of a range of different cosmetic formulations of the compounds of the present invention as described hereinabove, including their salts especially their zinc and/or copper salts to achieve and then maintain desired improvements in skin fairness, tone and quality required by users, depending on their different skin types, ages, ethnicities and life-styles such as extent of exposure to sunlight, and also on factors such as the season, time of year and fashion trends, the degree of skin lightening and skin quality enhancement desired, the speed and immediacy with which those improvements are required, and also on the extent to which the enhancements needs to be maintained once the desired skin fairness and quality has been achieved. This will be achieved by using a range of different cosmetic formulations containing different combinations of the different compounds of the present invention, and with the particular formulation used by any group or individual being selected based on the mechanisms of action of those ingredients best matching the changes in skin quality required by that group or individual. In addition, each formulation will be available in at least two forms that differ in activity, to be used depending on the extent to which the quality of the skin is required to be modified and the stage in the modification process so that for instance at the end of the process a low activity formulation can be continued to be used so as to just maintain the desired skin quality achieved.

In some embodiments, the present invention relates to a cosmetic or personal care composition comprising the homo and hetero-dimeric zinc/copper salts as described hereinabove for use in lightening and improving the tone and quality of skin, treating conditions such as acne, providing the skin health, wound-healing and anti-fungal benefits of zinc, and in achieving formulatory advantages such as shelf-life extension.

In some embodiments, the present invention relates to new cosmetic products containing the homo and hetero-dimeric zinc/copper salts as described hereinabove by the addition of the required individual homo or hetero-dimeric salts to the products; or with the new cosmetic products prepared following the formulation of creams containing one or more of maltol, saccharin/sodium saccharin, dehydroacetic acid, acesulphame and theobromine by the addition of a cosmetically acceptable soluble or insoluble source of zinc such as zinc hydroxide or sulphate, or zinc oxide respectively (Example 16).

In some embodiments, the present invention relates to a cosmetic or personal care composition comprising a combination of two or more compounds, each of the compounds containing the allylic or partially allylic carbonyl substructure of structure I as described hereinabove, in combination with one or more plant extracts. The plant extract includes, but not limited to, malt, ginseng, soybean, pine tree, coffee extracts containing maltol and cocoa extracts containing theobromine.

In some embodiments, the present invention relates to a cosmetic or personal care composition comprising a combination of two or more compounds, each of the compounds containing the allylic or partially allylic carbonyl substructure of structure I as described hereinabove, in combination with one or more plant extracts taken from Ayurveda, Jamu, Traditional Chinese Medicine or other Traditional Oriental Medicines.

In one embodiment, the present invention relates to the use of a range of cosmetic formulations of the compounds as described herein in single or multi-use forms such as capsules or in jar or tube containers and with different efficacies for use during the skin quality improving regime (Example 14).

In one embodiment, the present invention relates to the use of the compounds and combinations of the compounds in products as described herein, in products intended to lighten and/or improve the quality of skin including the lightening of pigmented spots.

In some embodiments, the present invention relates to a cosmetic or personal care composition comprising a combination of two or more compounds, each of the compounds containing the allylic or partially allylic carbonyl substructure of structure I as described hereinabove, for use in cosmetic or personal care products to enhance the fragrance of the cosmetic or personal care products. In one embodiment, the compounds include sodium saccharin, maltol and a 50:50 w/w blend of sodium saccharin and maltol that have aroma thresholds of 0.16%, 0.09% and 0.11% respectively in an oil-in-water cream. In another embodiment, aroma-less products can be formulated using the compounds and combinations of compounds as described herein at concentrations below their aroma thresholds, or by modifying the character of the fragrance of products containing the compounds and combinations of compounds as described herein by the addition of other extracts, fragrances or compounds including the addition of I-menthol, or aroma chemicals or aroma materials such as limonene, geraniol or rose oil essence.

In one embodiment, the present invention relates to the use of compounds and combinations of compounds as described herein to make products that have both skin lightening and other skin quality benefits including the lightening of pigmented spots, blemishes and areas such as age spots (senile lentigo) and/or to improve the skin tone by increasing a* and/or reducing b* rosy and yellow skin tone components, and/or by reducing fine lines and wrinkles, the intensity of pigmented spots, and/or improving skin radiance, softness, smoothness and elasticity (Examples 5, 6 and 7).

In one embodiment, the present invention relates to a cosmetic or personal care composition comprising a combination of two or more compounds, each of the compounds containing the allylic or partially allylic carbonyl substructure of structure I as described hereinabove, in combination with deodorants and/or antiperspirants for use in reducing microbial activity on the skin.

In one embodiment, the present invention relates to a cosmetic or personal care composition comprising a combination of two or more compounds, each of the compounds containing the allylic or partially allylic carbonyl substructure of structure I as described hereinabove for use in extending the shelf-lives of the cosmetic or personal care product (Example 8).

In one embodiment, the present invention relates to a cosmetic or personal care composition comprising a combination of two or more compounds, each of the compounds containing the allylic or partially allylic carbonyl substructure of structure I as described hereinabove, for use in reducing the viscosity of the cosmetic or personal care product. This is so as to be able to include high concentrations of active ingredients, such as the formulation of high concentrations of the skin lightener compounds as described herein so as to be active against pigmented spots that contain high concentrations of melanin (Example 10).

In one embodiment, the present invention relates to a cosmetic or personal care composition comprising a combination of two or more compounds, each of the compounds containing the allylic or partially allylic carbonyl substructure of structure I as described hereinabove, in particular, as their zinc salts as described herein for use in reducing colour formation in cosmetic or personal care products (Example 16).

In some embodiments, the present invention relates to compositions for preserving cosmetic, personal care, food, beverage and other products comprising compounds of the present invention, in particular, combinations of two or more compounds, each compound containing the allylic or partially allylic carbonyl substructure of structure I. In particular, the composition comprises maltol, dehydroacetic acid, canthaxanthin, saccharin, acesulphame, humulone, cohumulone, adhumulone, isohumulone, humulinic acid, lupulone, colupulone and adlupulone and their salts and combinations thereof. The invention further includes using the composition at concentrations in the products to be preserved, in particular, but not necessarily below the taste and aroma thresholds to prevent microbial growth and/or oxidation and the consequential spoilage of those products such as by microbial contamination and/or rancidification so as to lengthen their stability as safe products and thus their shelf-lives, and to replace the use of synthetic chemical preservatives such as parabens used in cosmetic and personal care products, and benzoic acid in food and beverage products (Example 8).

In accordance with an aspect of the invention, a method of regulating skin quality of a subject is provided. The method comprises the step of topically applying an effective amount of the cosmetic or personal care composition of the present invention on the skin of a subject.

In accordance with another aspect of the invention, a method of skin lightening is provided. The method comprises the step of topically applying an effective amount of the cosmetic or personal care composition of the present invention on the skin of a subject, for lightening of skin.

In various embodiments, the method comprises applying to the skin a cosmetic composition comprising two or more compounds including saccharin derivative and/or other compounds, each compound containing an allylic or partially allylic carbonyl substructure of structure I, in an amount of active per $cm^2$ of skin applied per application ranging from 0.001 $mg/cm^2$ to 0.38 $mg/cm^2$. In various embodiments, the amount of active per $cm^2$ of skin applied ranges from 0.001 $mg/cm^2$ to 0.30 $mg/cm^2$ per application. In various embodiments, the amount of active per $cm^2$ of skin applied ranges from 0.001 $mg/cm^2$ to 0.20 $mg/cm^2$ per application. In various embodiments, the amount of active per $cm^2$ of skin applied ranges from 0.001 $mg/cm^2$ to 0.10 $mg/cm^2$ per application. In various embodiments, the amount of active per $cm^2$ of skin applied ranges from 0.001 $mg/cm^2$ to 0.05 $mg/cm^2$ per application. In various embodiments, the amount of active per $cm^2$ of skin applied ranges from 0.001 $mg/cm^2$ to 0.01 $mg/cm^2$ per application.

In various embodiments, the method comprises applying a cosmetic or personal care composition of the present invention on the skin of a subject once a day, twice a day, thrice a day or once every two days.

In one embodiment, the regulating of the skin quality includes reducing endogenous and/or UV-induced melanogenesis, reducing activities of melanogenesis metabolic pathway and/or one or more of the signalling pathways that control the activity of the melanogenesis metabolic pathway, reducing the melanin content of the skin of the subject, and lightening of the skin, pigmented spots, freckles, blemishes and dark circles around the eyes of the subject.

(F) Method

In accordance with an aspect of the invention, a method of determining a composition for use in regulating or improving skin quality of a subject is provided. The method comprises measuring skin quality of a subject; identifying two or more compounds with melanogenesis inhibiting activities by selecting two or more compounds, each of the compounds containing an allylic or partially allylic carbonyl substructure having the following structure I:

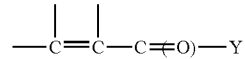

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—$CH_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$;
(ix) secondary amine-based group, —N(H)—; and
(x) amide-based group including —N(H)—C(=O)— or —N(H)—C(=O)—N(H)—; and preparing a formulation based on the measured skin quality so as to improve the skin quality using the identified compounds.

In accordance with another aspect of the invention, a method of determining a composition for use as a skin lightening agent is provided. The method comprises the steps of determining the skin type of a subject; identifying two or more compounds with melanogenesis inhibiting activities by selecting two or more compounds, each of the compounds containing an allylic or partially allylic carbonyl substructure having the following structure I:

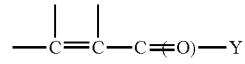

wherein Y is a second substructure immediately adjacent to the allylic or partially allylic carbonyl substructure and is selected from one of the following groups consisting of:
(i) hydroxyl-based group including —OH or —C(=)—(OH);
(ii) carbonyl-based group including —C(=)—C(=O)—$CH_3$;
(iii) ether group, —O—;
(iv) sultam group, —N(H)—S(=O)$_2$—;
(v) lactam group, —N(H)—C(=O)—;
(vi) apolar group including cyclic structures based on menthol or carotenoids;
(vii) secondary aldimine containing group including —N(H)—C(NH$_2$)=N— or —N(H)—C(H)=N—;
(viii) amine group, —NH$_2$,
(ix) secondary amine-based group, —N(H)—; and
(x) amide-based group including —N(H)—C(=O)— or —N(H)—C(=O)—N(H)—; and preparing a formulation based on the determined skin type of the subject using the identified compounds.

The combination of two or more compounds of the present invention with one or more sources of a divalent cation, in particular zinc and or copper such as one or more soluble zinc salts such as zinc sulphate, zinc chloride, zinc gluconate, zinc acetate, zinc pyrrolidone carboxylate, zinc glycinate or copper glucanate; or a sparingly soluble zinc salt such as zinc oxide especially when a slow formation of the zinc salt or salts of the compound or compounds of the present invention is required and/or when the sparingly soluble zinc salt also has a cosmetic benefit itself, such as zinc oxide that in particulate form has a UV protective effect or zinc ricinoleate that has deodorant properties, so that one or more homo-dimeric and/or hetero-dimeric zinc/copper salts of two or more of the compounds described herein are formed at concentrations suitable to achieve the desired effect or combination of effects as described herein.

Or the addition of a combination of one or compounds as described herein and defined by formula 1 with one or more sources of a divalent cation to a cosmetic or personal care formulation at a concentration suitable to achieve the desired effect or combination of effects as described herein.

To facilitate a better understanding of the present invention, the following examples of specific embodiments are given. In no way should the following examples be read to limit or define the entire scope of the invention. One skilled in the art will recognize that the examples set out below are not an exhaustive list of the embodiments of this invention.

EXAMPLES

Example 1

In-vivo skin lightening study on 28 Southeast Asian women and monitored by self-assessment, assessment by trained supervisors, and instrumentally was carried out. This double-blind CRO study proved the efficacy of maltol and sodium saccharin as skin lighteners, particularly when used as a cream containing a blend of 0.25% maltol and 0.25% sodium saccharin (NZW06, Tables I to III). A high quality lightened skin was produced, both as regards skin tone and other skin quality characteristics. A cream of the same composition, but containing 3.0% niacinamide (NZW01, Table II) instead of maltol and saccharin was used as a positive control.

The cream base used for blending the active ingredients contained the ingredients as follows: Aqua, *Butyrospermum parkii*, caprylic/capric triglyceride, C12-15 alkyl benzoate, cetearyl isononanoate, cyclomethicone, butylene glycol, hydroxyethyl acrylate, sodium dimethyl taurate copolymer, *Aloe barbadensis* leaf juice. The cream base was white in colour, with a pH range between 4.5 and 5.5.

The subjects were recruited and selected according to inclusion and exclusion criteria, as well as the prohibition and restriction concepts defined in the study protocol. In this study, 28 woman subjects were included by the Investigator. The age of the subjects was between 20 and 46 years old with the average age of 32.5 years.

The selected subjects were treated on two sides of the arms with the tested products. The tested products were identified and determined on which side of arm skin they should be applied. Subjects were briefed on how to use the tested products which they were required to use by themselves over the 28 days. The subjects were requested to avoid exposure to sunlight on their arm during the study period by wearing long sleeved clothing to cover up the test site, and to do so for a seven-day period before the study began. In the seven-day period before the study began, test subjects were also told to abstain from the application of any skincare products or cosmetic products.

Before application of the tested product, the skin melanin index was measured at all tested sites of arm skin in each subject. The measured area was marked for the next application and the next measurement. The tested product was applied twice daily, once in the morning and once in the evening, over 28 days on each site according to the determined sites. During this period, the subjects were monitored for their usage of the product every week in three ways:—

Skin melanin index was measured after 14 days of application and after 28 days of application. Three measurements were determined at the same site using Mexameter MX 18 and the mean value was calculated. In addition, the subjects were asked to fill a questionnaire on their perceptions on day 14 and day 28. The investigators were also asked to make observations each time the subject visited the clinic (i.e. on Day 7, 14, 21 and 28). The average data from all measurements was statistically analysed using the student t test using SPSS Statistic 20 to give results in three forms:— a. A skin melanin index for each test site (corresponding to each test product) on D0, D14 and D28,
b. A comparison result between the test products and the positive control, and
c. A comparison between the test products; which were found to be statistically significant at p<0.001 levels.

The main conclusions were that cream formulations containing maltol and/or sodium saccharin at an amount of 0.25% to 0.50% w/w were equally active in lightening the skins of the subjects as compared to the positive control formulation containing 3.0% w/w niacinamide. The cream containing a blend of 0.25% maltol and 0.25% saccharin (NZW 06) was preferred by the subjects, and the sample containing the 3.0% niacinamide (NZW 01) was least preferred.

Using the sample containing maltol and saccharin (NZW 06), 100% of the subjects observed and reported lightening of their skin by day 14 of the trial, with 74% noticing lightening by day 7. By comparison, only 82% of the subjects reported visible lightening by niacinamide by day 14 of the trial despite the use of a six-fold higher concentration of active ingredient. This result was confirmed when skin melanin index measurements were made using a Mexameter as the sample containing the blend of 0.25% maltol and 0.25% saccharin (NZW06) had specific activities 7.6 fold higher than the sample containing 3% niacinamide (NZW01) after use for 14 days, and 6.6 fold greater when used for 28 days (Table VI), and with these results statistically significant at p<0.001 levels. However, the most active samples at 14 days, and 28 days respectively were blends of 0.25% maltol with 1.5% niacinamide (NZW04), and a blend of 0.25% sodium saccharin and 1.5% niacinamide (NZW02, Table I to III).

In addition, the preferences of the subjects were assessed. The blend of 0.25% maltol and 0.25% saccharin (NZW06) was assessed as 82% positive, 18% neutral with no negative responses, and the 3% niacinamide sample (NZW01) was assessed as 64% positive, 25% neutral and 11% negative.

Tables I to III illustrate the skin lightening effects of the various compositions by measuring the difference of skin melanin index (SMI) at day 14 and day 28. Table IV shows the method of applying the cosmetic product containing the cosmetic composition. As shown in Table II, by comparing the results of NZW 01 and the other 3 combinations of products containing maltol and/or sodium saccharin, all 3 compositions yielded comparable SMI reduction to that obtained from 3% of niacinamide after 28-day applications. This statistically shows the superior specific activity of the products containing maltol and/or sodium saccharin in only an amount ranging from 0.25 wt % to 0.5 wt %, as compared to 3 wt % of NZW 01.

From these results, the cosmetic composition in NZW 06 was calculated to offer a 4-fold cost-in-use advantage as compared to niacinamide (see FIG. 1).

TABLE I

Influence Of Products On Skin Melanin Index For Products Containing Maltol, Sodium Saccharin, Niacinamide, or Combinations of the Compounds Compared To Baseline (n = 28)

| Product Code | Product | Skin Melanin Index (unit) ^ | | |
|---|---|---|---|---|
| | | Baseline | After 14 Days application | After 28 Days application |
| NZW 01 | Cream base containing Niacinamide at 3% | 280.68 ± 6.680 | 273.43 ± 6.369*** | 258.96 ± 5.920 **** |
| NZW 02 | Cream base containing Sodium Saccharin at 0.25% and Niacinamide at 1.5% | 293.07 ± 7.360 | 287.71 ± 7.433 ** | 266.21 ± 7.352 **** |
| NZW 03 | Cream base containing Maltol at 0.5% | 282.96 ± 7.583 | 274.96 ± 7.128 ** | 263.00 ± 6.921 **** |
| NZW 04 | Cream base containing Maltol at 0.25% and Niacinamide at 1.5% | 269.75 ± 5.795 | 260.11 ± 5.735 **** | 249.75 ± 5.376 **** |
| NZW 05 | Cream base containing Sodium Saccharin at 0.5% | 286.86 ± 6.714 | 277.64 ± 6.618 **** | 260.93 ± 6.218 **** |
| NZW 06 | Cream base containing Maltol and Sodium Saccharin at 0.25% each | 287.46 ± 7.469 | 278.29 ± 6.932 ** | 263.39 ± 6.686 **** |
| ctrl neg | Negative control (no treatment, measured in the same subjects and the same condition as the subject and condition for other tested products) | 258.07 ± 7.294 | 259.89 ± 7.338 | 277.82 ± 8.379 |

^ mean of 3 measurements ± SEM (Standard Error of the Mean)
* Statistically significant from baseline at $p < 0.05$
** Statistically significant from baseline at $p < 0.01$
*** Statistically significant from baseline at $p < 0.005$
**** Statistically significant from baseline at $p < 0.001$

TABLE II

Improvement In Skin Melanin Index For Products Containing Maltol, Sodium Saccharin, Niacinamide, or Combinations of the Compounds As Opposed To Positive Control Containing 3% Niacinamide

| Product Code | Product | Skin Melanin Index (unit) ^ | | |
|---|---|---|---|---|
| | | Baseline | After 14 Days application | After 28 Days application |
| NZW 01 | Cream base containing Niacinamide at 3% | 280.68 ± 6.680 | −7.250 ± 2.625 *** | −21.714 ± 3.473 **** |
| NZW 02 | Cream base containing Sodium Saccharin at 0.25% and Niacinamide at 1.5% | 293.07 ± 7.360 | −5.357 ± 2.159 ** | −26.857 ± 2.379 **** |
| NZW 03 | Cream base containing Maltol at 0.5% | 282.96 ± 7.583 | −8.000 ± 3.092 ** | −19.964 ± 2.980 **** |
| NZW 04 | Cream base containing Maltol at 0.25% and Niacinamide at 1.5% | 269.75 ± 5.795 | −9.643 ± 2.410 **** | −20.000 ± 2.238 **** |
| NZW 05 | Cream base containing Sodium Saccharin at 0.5% | 286.86 ± 6.714 | −9.214 ± 2.756 **** | −25.929 ± 3.188 **** |
| NZW 06 | Cream base containing Maltol and Sodium Saccharin at 0.25% each | 287.46 ± 7.469 | −9.179 ± 3.500 ** | −24.071 ± 3.852 **** |

−a negative sign refers to a reduction in Skin Melanin Index, i.e. indicating lightening occurring.
^ mean of 3 measurements ± SEM (Standard Error of the Mean)
* "Statistically significant from baseline at $p < 0.05$
** Statistically significant from baseline at $p < 0.01$
*** Statistically significant from baseline at $p < 0.005$
**** Statistically significant from baseline at $p < 0.001$

TABLE III

Comparison Of The Change In Skin Melanin Index Between Products Containing Maltol, Sodium Saccharin, Niacinamide, or Combinations of the Compounds Versus Positive Control Containing 3% Niacinamide

| | | | Difference in the Skin Melanin Index (unit) | |
|---|---|---|---|---|
| Products to be compared | | | Product (Day 14-Day 0) - Product (Day 28-Day 0) - | |
| Product Code | Product | Positive Control | Positive Control (Day 14-Day 0) | Positive Control (Day 28-Day 0) |
| NZW 02 | NZW 02 - Cream base containing Sodium Saccharin at 0.25% and Niacinamide at 1.5% | Cream base containing Niacinamide at 3% | 1.89 ± 2.68 | −5.11 ± 3.84 |
| NZW 03 | Cream base containing Maltol at 0.5% | | −0.78 ± 3.25 | 1.78 ± 3.46 |
| NZW 04 | Cream base containing Maltol at 0.25% and Niacinamide at 1.5% | | −2.39 ± 3.12 | 1.75 ± 3.54 |
| NZW 05 | Cream base containing Sodium Saccharin at 0.5% | | −1.96 ± 3.83 | −4.18 ± 4.25 |
| NZW 06 | Cream base containing Maltol and Sodium Saccharin at 0.25% each | | −1.93 ± 4.39 | −2.32 ± 4.83 |

−a negative sign indicates that the product achieved a greater skin melanin index reduction as compared to the positive control

TABLE IV

Method of Applying the Products Containing the Cosmetic Composition

| | |
|---|---|
| Application Area | Left and right arm skin facing medial to the body |
| Quantity Applied | 0.16 g to 0.21 g /usage/tested area |
| Concentration Applied | As is (100%, without dilution) |
| Frequency | Twice daily, morning and evening Note: if subject showers in the morning or evening, application of test material should always be done after shower |
| Usage | Apply each product to each tested area which have been determined previously |
| Duration of Application | 28 Days |
| Tested area | approximately 60 cm$^2$ |

Table V illustrates the ranking of the various compositions from best to worst based on user satisfaction measurements. The questionnaire was formulated to include the questions such as: 1) what were your first impressions after application of the various compositions? 2) How quickly do you expect to see a lightening effect? 3) Are you satisfied with the quality of skin lightening achieved? 4) How many days after the first application of the various compositions did you observe a lightening effect? 5) are you satisfied with the quality of skin lightening achieved? 6) How many days after the first application of the test product did you observe a lightening effect?

TABLE V

Results of user satisfaction measurements after applying various compositions

| | Number of Subject (%) Answered on various compositions | | | | | |
|---|---|---|---|---|---|---|
| Ranking | NZW 06 Cream base containing Maltol and Sodium Saccharin at 0.25% each | NZW 05 Cream base containing Sodium Saccharin at 0.5% | NZW 04 ream base containing Maltol at 0.25% and Niacinamide at 1.5% | NZW 03 Cream base containing Maltol at 0.5% | NZW 02 Cream base containing Sodium Saccharin at 0.25% and Niacinamide at 1.5% | NZW 01 Positive Control Cream base containing Niacinamide at 3% |
| 1 | 29 | 14 | 7 | 11 | 14 | 25 |
| 2 | 7 | 39 | 18 | 18 | 14 | 4 |
| 3 | 18 | 7 | 29 | 14 | 11 | 21 |
| 4 | 21 | 11 | 14 | 32 | 14 | 7 |
| 5 | 14 | 21 | 11 | 4 | 39 | 11 |
| 6 | 11 | 7 | 21 | 21 | 7 | 32 |
| Total | 100 | 100 | 100 | 100 | 100 | 100 |

Specific activity was obtained as follows. Specific activity is the skin melanin index (SMI) reduction per gram of accumulated actives applied at a time point. It has been calculated in the following manner;

$$\text{Specific activity} = \frac{\Delta SMI\ T_x}{\Sigma\ \text{Active Compound}_{mg} T_x}.$$

TABLE VI

Comparison of Specific Activity Between Products Containing Maltol, Sodium Saccharin, Niacinamide, or Combinations of the Compounds Versus Positive Control Containing 3% Niacinamide

| Product Code | Product | Day 14 Accumulated actives applied (g) | Day 14 Specific Activity | Day 28 Accumulated actives applied (g) | Day 28 Specific Activity |
|---|---|---|---|---|---|
| NZW 01 | Cream base containing Niacinamide at 3% | 0.148 | 49.04 ± 17.76 | 0.319 | 68.03 ±10.88 |
| NZW 02 | Cream base containing Sodium Saccharin at 0.25% and Niacinamide at 1.5% | 0.089 | 59.74 ± 24.08 | 0.189 | 142.00 ± 12.58 |
| NZW 03 | Cream base containing Maltol at 0.5% | 0.025 | 315.71 ± 122.02 | 0.053 | 371.35 ± 55.43 |
| NZW 04 | Cream base containing Maltol at 0.25% and Niacinamide at 1.5% | 0.080 | 120.00 ± 29.99 | 0.171 | 117.29 ± 13.12 |
| NZW 05 | Cream base containing Sodium Saccharin at 0.5% | 0.024 | 378.24 ± 113.14 | 0.052 | 503.28 ± 61.88 |
| NZW 06 | Cream base containing Maltol and Sodium Saccharin at 0.25% each | 0.025 | 370.42 ± 141.24 | 0.052 | 464.69 ± 74.36 |

Example 2

As part of the same study that was carried out in Example 1, data was collected and the skin lightening effects on the 28 subjects were observed as follows.

Data were collected from the 28 subjects who were each treated with 3 test samples consisting of (i) maltol ("M"); (ii) sodium saccharin ("S"); and (iii) a combination of maltol and sodium saccharin ("M+S") for 28 days. The data were collected on Day 14 and Day 28.

The 28 subjects were firstly classified into three categories: 'Got darker' [SMI>0]; 'No change' [SMI=0]; 'Got lighter' [SMI<0]). The results obtained were as follows:

TABLE VII

| Product Code | 'Got darker' [SMI > 0] | No change' [SMI = 0] | 'Got lighter' [SMI < 0]) |
|---|---|---|---|
| M14 | 7 | 0 | 21 |
| M28 | 3 | 0 | 25 |
| S14 | 4 | 2 | 22 |
| S28 | 0 | 0 | 28 |

TABLE VII-continued

| Product Code | 'Got darker' [SMI > 0] | No change' [SMI = 0] | 'Got lighter' [SMI < 0]) |
|---|---|---|---|
| M + S14 | 9 | 1 | 18 |
| M + S28 | 2 | 0 | 26 |

For those subjects whose skin got lighter, the degree of SMI reduction was also obtained, subdivided into categories, where the values represent SMI reductions. Data presented below were cumulative, i.e. as the magnitude of SMI reduction increased, the number of subjects was a subset of those in the previous (lower SMI reduction) category. The results obtained were shown in the Table VIII below.

TABLE VIII

| | SMI reduction | | | | | | | | | | | |
|---|---|---|---|---|---|---|---|---|---|---|---|---|
| | <0 | <5 | <10 | <15 | <20 | <25 | <30 | <35 | <40 | <45 | <50 | <55 |
| M14 | 21 | 14 | 11 | 6 | 5 | 3 | 3 | 2 | 2 | 1 | 0 | 0 |
| M28 | 25 | 25 | 21 | 17 | 13 | 10 | 5 | 4 | 2 | 2 | 2 | 1 |
| S14 | 22 | 16 | 10 | 8 | 6 | 4 | 2 | 2 | 0 | 0 | 0 | 0 |
| S28 | 28 | 28 | 22 | 18 | 15 | 14 | 9 | 8 | 5 | 5 | 3 | 3 |
| M + S14 | 18 | 14 | 9 | 9 | 6 | 6 | 5 | 3 | 2 | 2 | 1 | 0 |
| M + S28 | 26 | 24 | 19 | 18 | 14 | 10 | 9 | 7 | 7 | 6 | 3 | 3 |

The above results show that for maltol (M), sodium saccharin (S) and a combination of maltol and sodium saccharin (M+S), SMI reductions were larger at the 28-day time point than at the 14-day time point. Further analysis on the 28-day time point data was then carried out. The goal of the analysis was to determine whether a combination of the two active ingredients, maltol and sodium saccharin, was more effective in reducing SMI than the individual active ingredients.

A linear regression analysis method was selected for the analysis. The $R^2$ statistic is based on the distances of individual data points from the linear regression (best fit line), and has values between 0 and 1. $R^2$ provides a measure of the proportion of the variability in the data that the factor of interest accounts for. The significance level was set at 5% (i.e. P values<0.05 are considered to indicate a significant difference between groups).

The first comparison was made between the degree of SMI reduction with the combination of maltol and sodium saccharin and the mean SMI reduction for those treated with maltol or sodium saccharin alone. The mean values for maltol (M) or sodium saccharin (S) are:

TABLE IX

Mean values for Maltol (M) or Sodium Saccharin (S)

| | | |
|---|---|---|
| <0:26.5 | <20:14 | <40:3.5 |
| <5:26.5 | <25:12 | <45:3.5 |
| <10:21.5 | <30:7.0 | <50:2.5 |
| <15:17.5 | <35:6.0 | <55:2.0 |

Figure 8:
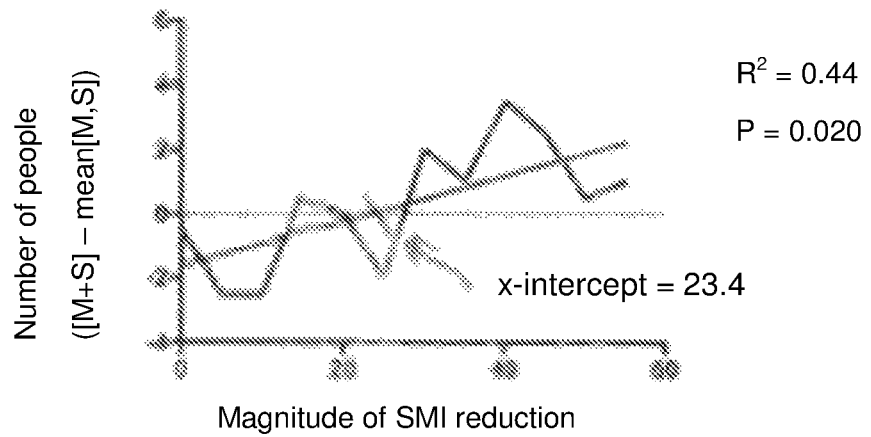
FIG. 8 is a linear regression graph comparing the degree of skin melanin index (SMI) reduction with the usage of maltol and sodium saccharin (M+SS) versus the mean SMI reduction for those using M or SS alone. The difference in the number of people between M+S versus mean (M or S) was calculated for each SMI reduction category, namely (<0, <5, <10, <15, <20, <25, <30, <35, <40, <45, <50, <55) at the 28-day time point.

The difference in the number of people between M+S as compared to mean (M or S) was calculated for each SMI reduction category. A linear regression of these data produced a line with positive slope, an $R^2$ value of 0.44 and a P value of 0.020 (see FIG. 8). The x-intercept of the regression line was at SMI=23.4.

Further analysis was carried out to compare the SMI reduction between M+S and M alone or S alone.

Figure 9:
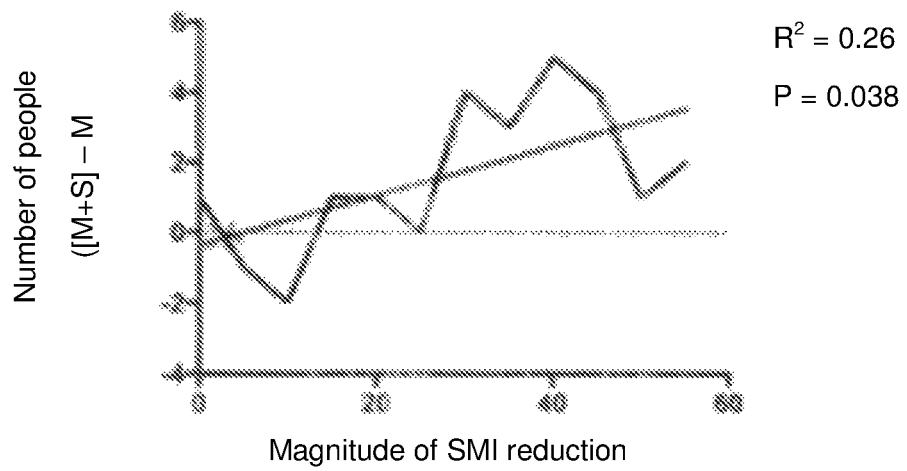
FIG. 9 is a linear regression graph comparing the degree of skin melanin index (SMI) reduction with the usage of maltol and sodium saccharin (M+SS) versus the mean SMI reduction for those using M alone. The difference in the number of people between M+S versus M was calculated for each SMI reduction category, namely (<0, <5, <10, <15, <20, <25, <30, <35, <40, <45, <50, <55) at the 28-day time point.

FIG. 9 shows the comparison between M+S and M alone, with the difference in number of people between M+S and M alone plotted against the magnitude of SMI reduction. A linear regression of these data produced a line with positive slope, an $R^2$ value of 0.26 and a P value of 0.038. The x-intercept of the regression line was at SMI=5.1.

Figure 10:
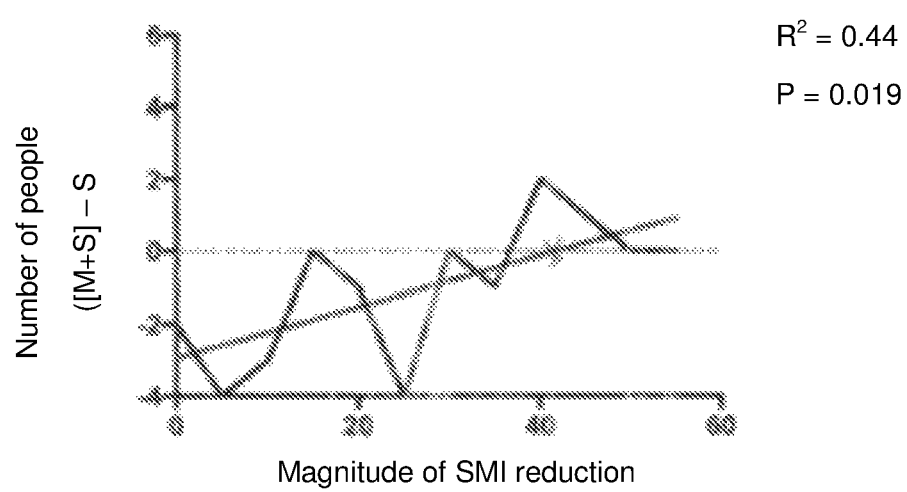
FIG. 10 is a linear regression graph comparing the degree of skin melanin index (SMI) reduction with the usage of maltol and sodium saccharin (M+SS) versus the mean SMI reduction for those using SS alone. The difference in the number of people between M+S versus SS was calculated for each SMI reduction category, namely (<0, <5, <10, <15, <20, <25, <30, <35, <40, <45, <50, <55) at the 28-day time point.

FIG. 10 shows the comparison between M+S and S alone. The difference in the number of people between M+S and S alone is plotted for each SMI reduction category. A linear regression of these data produced a line with positive slope, with an $R^2$ value of 0.44 and a P value of 0.019. The x-intercept of the regression line was at SMI=41.8.

Conclusions

The P value for the linear regression analysis indicates that there is a significant difference between M+S and mean (M or S) in terms of SMI reduction. The x-intercept of the linear regression at SMI=23.4 indicates that more people had larger SMI reductions with M+S as compared to the mean of M or S alone.

Breaking this down into comparison of M+S with M alone or S alone, again there was a significant difference for M+S as compared to M or S. In the comparison between M+S and M, the x-intercept of the linear regression was SMI=5.1, indicating that more people had larger SMI reductions with M+S than with M alone. In contrast, in the comparison between M+S and S alone, the linear regression had an x-intercept of 41.8, indicating that fewer people had smaller SMI reductions with M+S than with S alone. Overall, the above analyses suggest that maltol (M) and saccharin (S) may have additive effects on SMI reduction.

Example 3

In-Vitro Melanogenesis Inhibition Evaluation

The melanogenesis inhibiting activity of next cohort of compounds as measured in B16 cultured melanocyte cells was evaluated, using kojic acid as a positive control, and compared to maltol and sodium saccharin whose in-vivo activities are already proven in Example 1:

TABLE X

IC50 of skin lightening actives tested in
B16 cell melanogenesis inhibition assays.

| | IC50 (g/l) |
|---|---|
| Acetylsalicylic Acid | 0.262 |
| Inosine Monophosphate (IMP) | 0.227 |
| Uracil | 0.143 |
| SS + Guanine | 0.141 |
| SS + Citrazinic Acid | 0.137 |
| Isatoic Anhydride | 0.132 |
| TB + ASK | 0.131 |
| SS + ASK | 0.119 |
| IMP + SS | 0.117 |
| SS + TB | 0.108 |
| M + SS + TB | 0.101 |
| Phthalimide | 0.089 |
| IMP + M | 0.086 |
| Citrazinic Acid | 0.077 |
| Erythorbic Acid | 0.073 |
| Dehydroacetic Acid (DHAA) | 0.073 |
| Hypoxanthine | 0.07 |
| Maltol (M) | 0.065 |
| Ethyl Maltol | 0.059 |
| Acesulphame K (ASK) | 0.058 |
| SS + DHAA | 0.057 |
| Guanine | 0.056 |
| Sodium Saccharin (SS) | 0.055 |
| M + SS | 0.046 |
| Theobromine (TB) | 0.037 |
| M + TB | 0.037 |
| Kojic acid (Standard) | 0.051 |

Melanogenesis inhibiting activities were obtained as follows. B16 melanocyte cells were cultured in a T75 flask and allowed to grow to a high confluency. The appropriate volumes of compounds were added into the 24 well-plates. Cells were dislodged from the T75 flask and counted using a haemocytometer. Fresh DMEM (phenol red-free) containing 10% FBS was added to dilute the cells to an appropriate density, $0.025 \times 10^6$ cells for a 24 well-plate. Cells were aspirated and transferred accordingly into the wells, each containing different compounds of varying concentrations, specifically 25 µM, 75 µM, 100 µM, 200 µM and 300 µM. The 24 well-plates were then incubated for 3 days. After the treatment, the wells were washed with PBS and 1M NaOH solution was added into each well and incubated at 37° C. for 2 hours, to lyse the cells to allow full release of the melanin. Optical densities (ODs) were measured at 480 nm using a BioTek Synergy HTX multi-mode reader. The results were automatically recorded in an excel spreadsheet.

Example 4

Cytotoxicity activities to determine cell viability were obtained as follows. B16 melanocyte cells were plated in a 24 well-plate one day before the actual assay. Fresh DMEM (with phenol red) containing 10% FBS was added to dilute the cells to an appropriate density, $0.025 \times 10^6$ cells for a 24 well-plate. 1 ml of the DMEM with 10% FBS was added to each well. The cells in each well were treated with appropriate concentration of compounds (i.e. 75 µM, 100 µM and 300 µM). The well-plate with treated cells were then left in the incubator at 37° C., 5% $CO_2$ for approximately 16 hours overnight. The media was removed and 1 ml of PBS solution was added into each well to wash and remove the colour of the phenol red in the DMEM. Then, 1 ml of fresh PBS was added into each individual well. 15 µl of the prepared Resazurin stock solution was added (8 µg/ml) into each well containing the compounds. The Resazurin stock solution was prepared by adding 800 µg of Resazurin sodium salt in 10 ml of PBS (pH 7.4) to make a concentration of 80 µg/ml, which was further diluted by adding 0.1 ml of the 80 µg/ml solution to 0.9 ml of PBS to make 8 µg/ml of stock solution. The well-plates were incubated at 37° C. for 2 hours. The plate was immediately read, after 2 hours, using a BioTek Synergy HTX multi-mode reader at an emission and excitation wavelength of 600 nm and 528 nm respectively, with a gain of 35. The results were automatically recorded in an excel spreadsheet.

Figure 11:
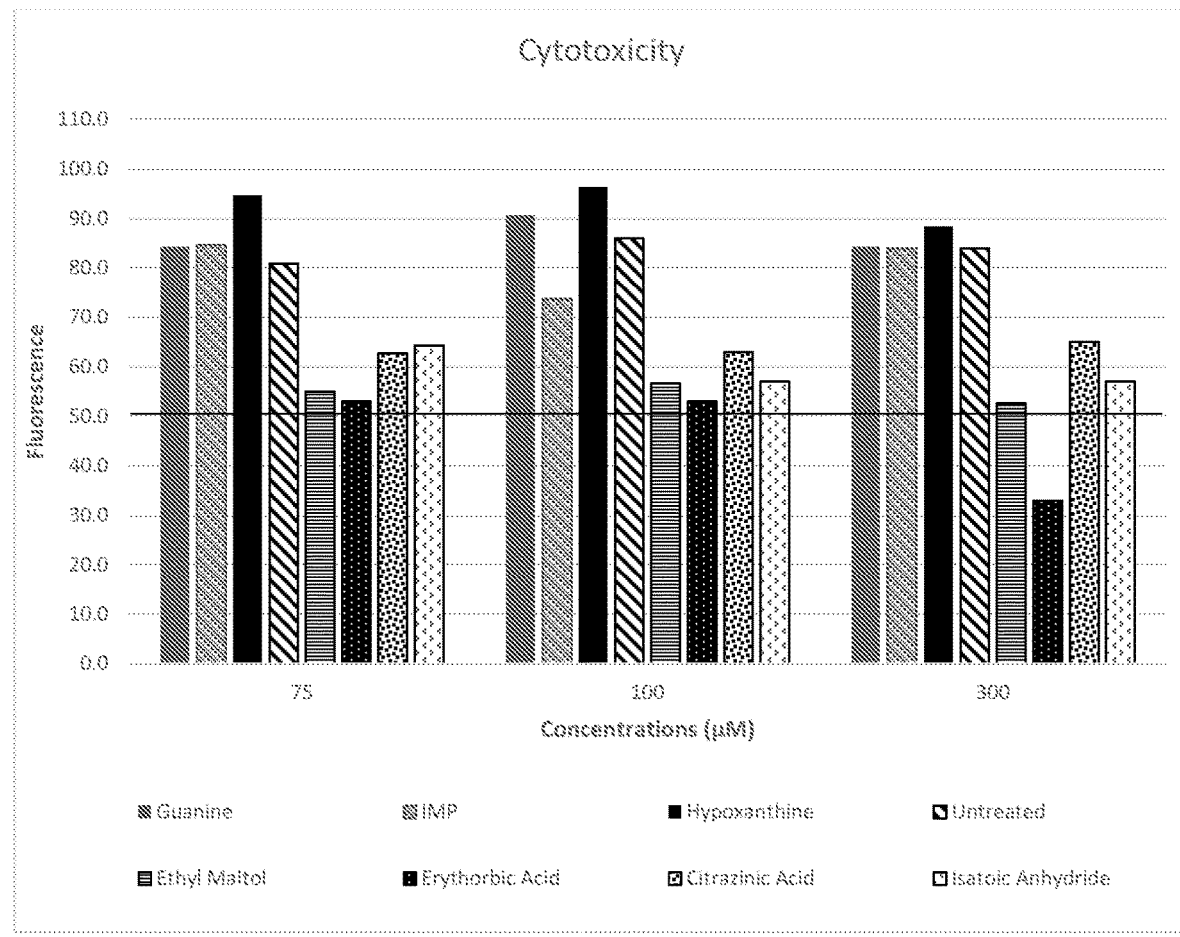
FIG. 11 is a chart showing the results of the cytotoxicity tests carried out on some of the compounds of the present invention, based on fluorescence, at various concentrations of 75 μM, 100 μM and 300 μM.

FIG. 11 shows the result of the cytotoxicity tests of the compounds on the B16 melanocytes. To assess the sufficient cell viability of the B16 cells upon reaction with the compounds at various concentrations, a fluorescence value greater than 50 is required. From the results obtained, most of the compounds had a fluorescence value of 50 and above except for ethyl maltol which resulted in cell toxicity at concentrations greater than 100 µM. This suggests that the compounds do not cause a great loss in cell viability and that the reduction in melanin is not due to loss in cell viability but due to melanogenesis inhibition.

Example 5

Skin Tone Measurements

Figure 2:
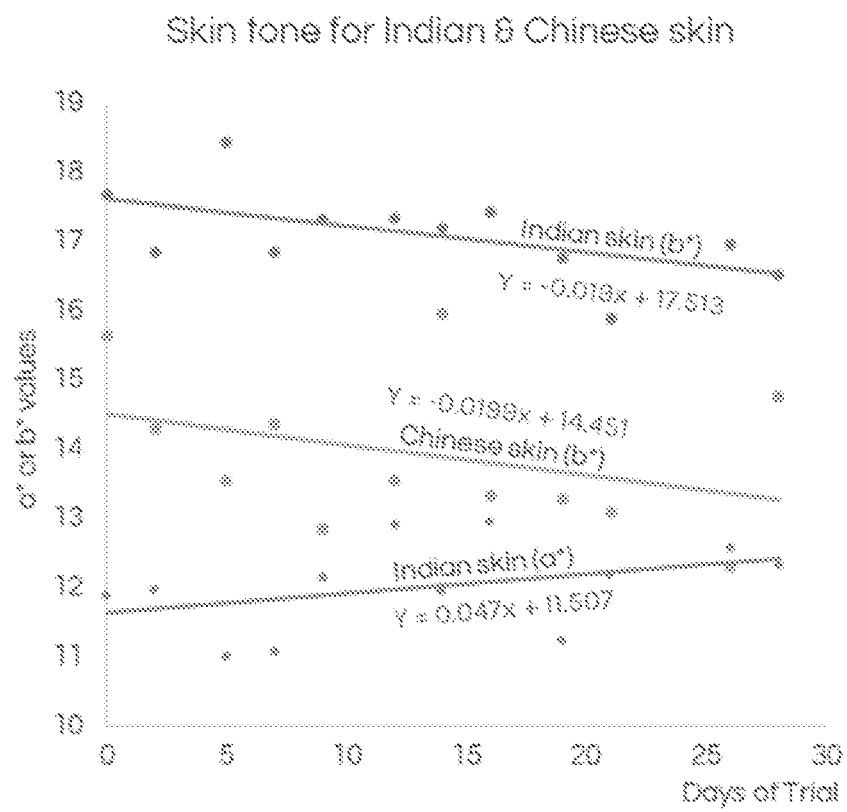
FIG. 2 shows the relationship between the improvement of skin tone over time in a trial application of the product composition containing maltol and sodium saccharin.

FIG. 2 shows the improvement on skin tone after applying the cream containing 0.25% maltol and 0.25% saccharin twice daily for 28 days. The a* (rosy-red tone) and b* (yellow tone) components of the skin tone were monitored.

The cream base used for blending the active ingredients contained the ingredients as follows: Aqua, *Butyrospermum parkii*, caprylic/capric triglyceride, C12-15 alkyl benzoate, cetearyl isononanoate, cyclomethicone, butylene glycol, hydroxyethyl acrylate, sodium dimethyl taurate copolymer, *Aloe barbadensis* leaf juice. The cream base was white in colour, with a pH range between 4.5 and 5.5.

Over the 28-day period, the a* (rosy-red tone) component of Indian skin increased, and the b* (yellow tone) component of Indian and Chinese skins decreased. For comparison, the widely used skin lightener niacinamide had diametrically opposite effects on Chinese skin and especially on Indian skin. Before starting the study, all subjects' melanin index, L*a*b* and ITA value were measured at the tested site using Mexameter MX18 and Courage+Khazaka (CK) Colorimeter CL 400. Photos and instrument measurements were taken at the start of the testing (Day 0), during the testing (D2, D5, D7, D9, D12) and after the testing (D14, D21 and D28). The materials were applied twice daily, once in the morning and once in the evening (if the subject was to shower in the morning or the evening, the test material was applied after the shower) to intact skin of the arm for 14 days. Each subject applied 5 products on the left arm. Subjects wore an arm sleeve over part of the right arm for the occluded site, so as to provide 2 negative controls, one occluded from light and UV-radiation (right arm) and one covered under fabric (left arm) so as to understand the effect of melanogenesis even when no light is passing through. The tested areas were evaluated on their skin melanin index, L*a*b* and ITA after D2, D5, D7, D9, D12, D14, D21 and D28 of application using Mexameter MX 18 and CK Colorimeter CL400.

Example 6

Skin Quality Analysis

As part of the same experiment above, general skin quality effects were also observed. Over the 28 days, the skins of the Indian and Chinese subjects became brighter, smoother and more youthful looking.

Example 7

Further Skin Quality Analysis Study

This analysis was carried out using the IOMA™ Micro Electro Mechanical Systems (MEMS) technology to photographically analyse the condition of the skin. It provides details of 12 different attributes, hydration, desquamation, fine lines, wrinkles, sagging, redness, UV damage, bacterial activity, clogged pores, bags and eyelids, and dark circles and line lines around eyes. Each of the conditions was measured on a scale of 1-15, with 1 being the ideal. The rationale of this further analysis was to gain independently assessed data for the efficacy of a cream containing 1.5% maltol and 1.5% sodium saccharin applied to the face. This was done using a subject who had been using a high quality commercial cosmetic product on a daily basis for several years previously, and who continued to use this product as well as the cream containing 1.5% maltol and 1.5% saccharin during the trial. The commercial product (SK-II™ Facial Wash) contained water, glycerin, Galactomyces ferment filtrate, niacinamide, butylene glycol, sucrose polycottonseedate, isopropyl isostearate, isohexadecane, dimethicone, cetyl alcohol, polyacrylamide, panthenol, polymethylsilsesquioxane, tocopheryl acetate, stearyl alcohol, C13-14 isoparaffin, benzyl alcohol, methylparaben, dimethiconol, PEG-100 stearate, stearic acid, disodium EDTA, laureth-7, propylparaben, cetearyl alcohol, cetearyl glucoside, ethylparaben, fragrance, sodium hydroxide, *Saccharomyces cerevisiae* extract, palmitoyl dipeptide-7 and hexapeptide-3.

During the trial, the cream containing 1.5% maltol and 1.5% saccharin was applied to the face, particularly to the skin underneath the eyes, every morning. 0.5 g of the cream was applied on the left side of the face and 0.4 g was applied on the right side of the face. The subject first patted the cream on the sides of the face, followed by massaging the cream into the sides of the face, on the cheeks, but particularly on the upper cheekbone and under the eye area, with the remainder of the cream being applied onto the forehead but not on the nose. The cream base used for blending the active ingredients contained the following ingredients: Aqua, disodium EDTA, Ultrez-20, glycerine, methyl gluceth-20, PEG-20 methyl glucose sesquistearate, isopropyl isostearate/isopropyl myristate, Tween 20, and NaOH. The cream base was white in colour, with a pH ranges between 6 and 7. IOMA instrumental assessments were made on Day 0, Day 14, Day 28 and Day 135, and the imaging was carried out in the late afternoon. After 28 days, a 60% reduction in dark circles around the eyes, and a 54% reduction in fine lines around the eyes were observed. After 4.5 months of using the cream, a re-examination showed that improvements to the reduction of dark circles and fine lines around the eyes had continued. The reduction in fine lines was also apparent elsewhere on the skin. Cell regeneration on the face was enhanced and UV damage was reduced.

Figure 3:
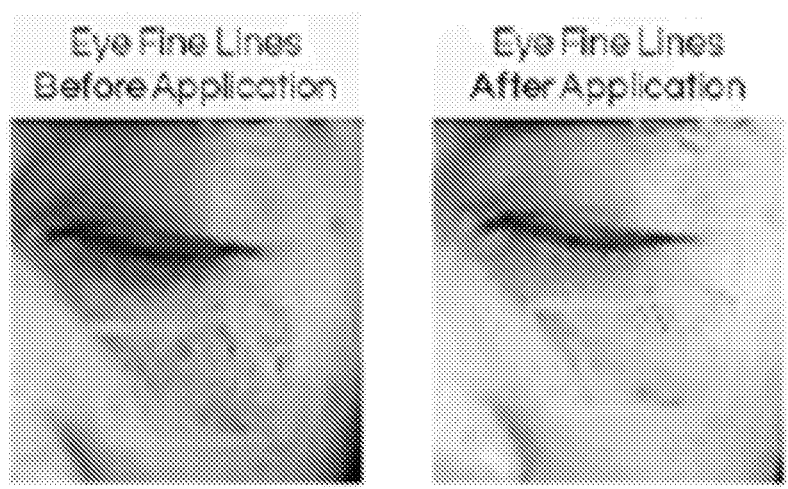
FIG. 3 shows the effect of a product composition containing maltol (1.5%) and sodium saccharin (1.5%) on the dark circles and fine lines around the eyes after 28 days of application.

FIG. 3 shows the effect of the cream containing 1.5% maltol and 1.5% sodium saccharin on dark circles and fine lines around eyes after 28 days of application. The experimental results show that there was a 60% improvement in decreasing dark circles around the eyes and 54% improvement in decreasing fine lines around the eyes. This is despite the subject being a regular long-term user of the SK-II facial wash. The significant improvements observed were in addition to those which had already been achieved.

TABLE XI

| 100 = Ideal | Day 0 | Day 14 | Day 28 | | Overall Improvement by: |
|---|---|---|---|---|---|
| Dark circles | 27/100 | 73/100 ↑ | 87/100 ↑ | → | ↑ 60% |
| Eye fine lines | 13/100 | 67/100 ↑ | 67/100 ↔ | → | ↑ 54% |

Data collected using a commercial unit; 100 being the ideal skin condition

Example 8

Antimicrobial Activity

Figure 4:
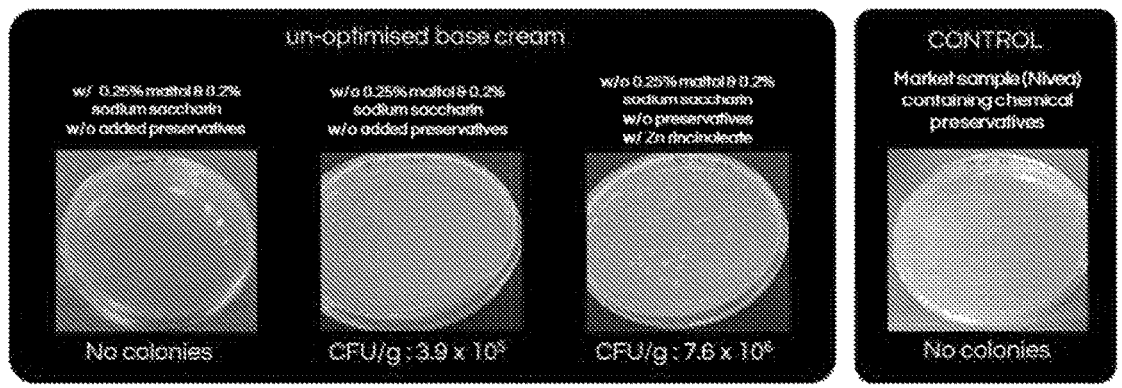
FIG. 4 shows the antimicrobial activities of maltol and saccharin together on the shelf-life stability of various compositions over a period of 28 days.

FIG. 4 shows the result of antimicrobial activity in the samples.

To assess resistance to microbial contamination, a cream containing 0.25% maltol and 0.25% sodium saccharin (NZW 06) was inoculated with $10^5$-$10^6$ CFU/ml *Pseudomonas aeruginosa* and incubated at 37° C. for 28 days (with reference to ISO 11903 method). The cream base used for blending the active ingredients contained the ingredients as follows: Aqua, disodium EDTA, Ultrez-20, glycerine, methyl gluceth-20, PEG-20 methyl glucose sesquistearate, isopropyl isostearate/isopropyl myristate, Tween 20, and NaOH. The cream base was white in colour, with a pH range between 6 and 7. Market sample (Nivea) containing chemical preservatives was chosen as the control.

At the end of this period, it was observed that the control sample contained $3.9\times10^5$ CFU/ml, but both the cream containing maltol and sodium saccharin (NZW 06), and the market sample containing chemical preservatives were entirely free of microbial colonies. This suggests that the product containing NZW 06 does not require additional chemical preservatives. This therefore saves on formulation costs, and allows for preservative-free consumer claims to be made.

Both sodium saccharin and maltol, when tested individually at 0.05% completely inhibited the growth of *P. aeruginosa*.

Example 9

Colour and Stability Test

Figure 5:
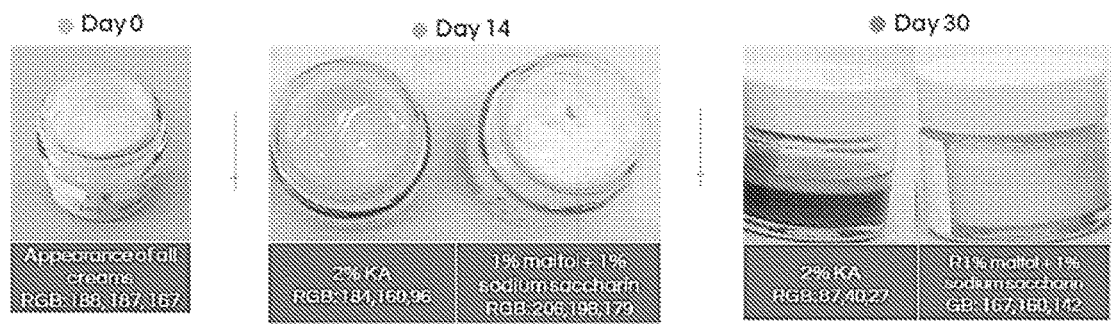
FIG. 5 shows the colour and emulsion stability of the various test samples after 30 days of storage at 45° C.

The appearance such as the colour of the product containing 1 wt % maltol and 1 wt % sodium saccharin was evaluated (FIG. 5) via a colour and physical stability trial. A blended composition (2 wt % BC containing 1 wt % maltol and 1 wt % sodium saccharin) was stored in the oven at 45° C. for 30 days, together with a control containing 2 wt % of kojic acid (KA). The accelerated colour generation was monitored via image taking as well as RGB (Red, Green, Blue) analysis, where a pure white colour represents (255, 255,255).

The cream base used for blending the active ingredients contained the ingredients as follows: Aqua, *Butyrospermum parkii*, caprylic/capric triglyceride, C12-15 alkyl benzoate, cetearyl isononanoate, cyclomethicone, butylene glycol, hydroxyethyl acrylate, sodium dimethyl taurate copolymer, *Aloe barbadensis* leaf juice. The cream base was white in colour, with a pH ranges between 4.5 and 5.5. At the start of the trial, the test creams had RGB values of (188, 187, 167).

It was observed at the end of the trial that the cream containing 2 wt % KA was found to darken from white colour to dark yellow and finally to dark brown with a RGB value of (87,40,27). It also turned watery upon prolonged storage at 45° C. On the contrary, the appearance and texture of the cream containing 2 wt % BC was well maintained with only very slight discoloration, with RGB readings of (167,160,142). This provides advantages of sales and storage of the creams in tropical climates or in the summer where there exists a high demand for skin lightening and skin quality products.

Example 10

Rheological properties of the creams with different cosmetic compositions were evaluated based on viscosity measurements. The individually tested samples were dissolved in a base cream (control) with a viscosity of 25,000 mPa·s. The cream base used for blending the active ingredients contained the ingredients as follows: Aqua, Butyrospermum parkii, caprylic/capric triglyceride, C12-15 alkyl benzoate, cetearyl isononanoate, cyclomethicone, butylene glycol, hydroxyethyl acrylate, sodium dimethyl taurate copolymer, Aloe barbadensis leaf juice. The cream base was white in colour, with a pH ranges between 4.5 and 5.5.

Figure 6:
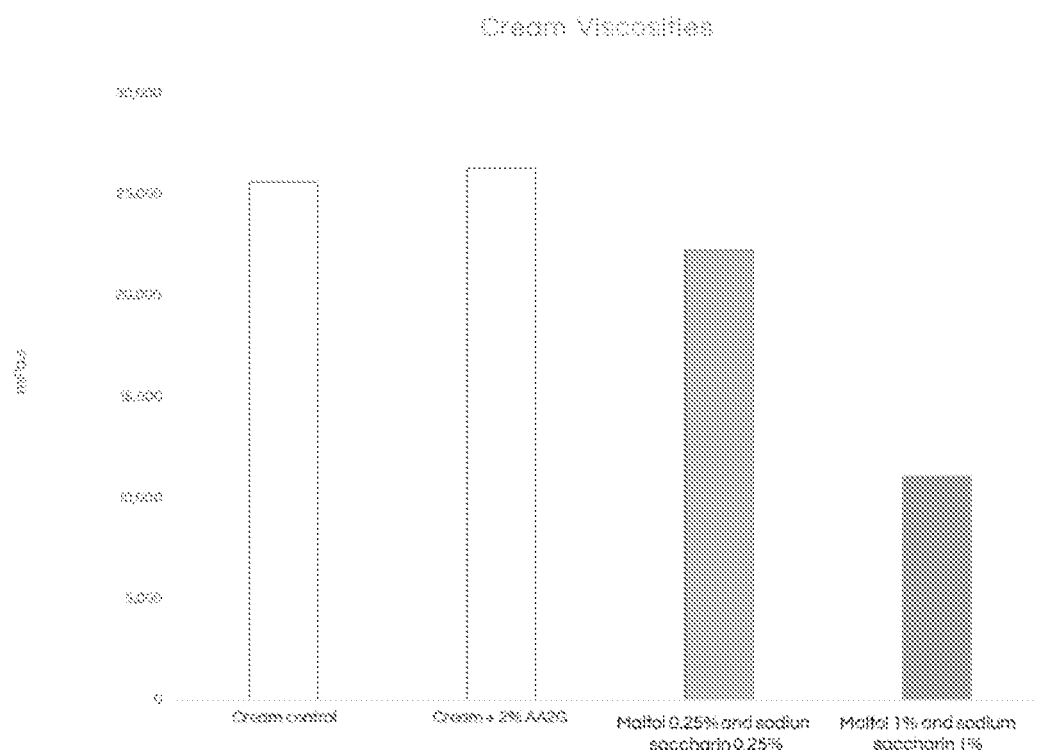
FIG. 6 shows the effects of maltol and sodium saccharin on the viscosities of various formulatory compositions.
Figure 7:
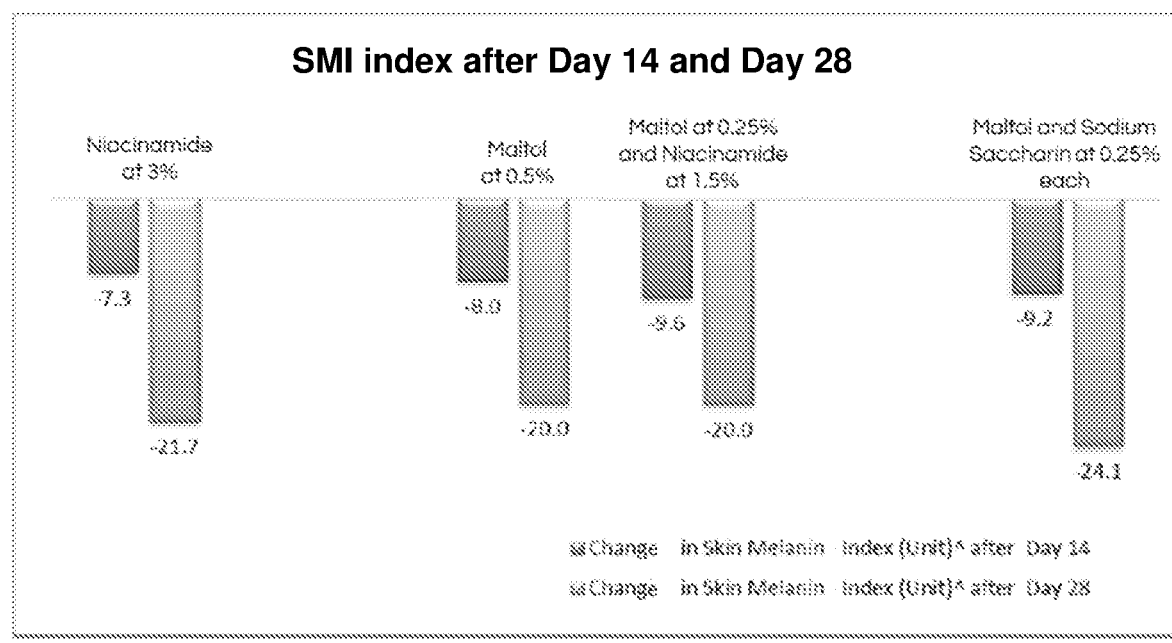
FIG. 7 shows the improvement of various compositions on changes in the skin melanin index over 14 and 28 days.

When maltol and sodium saccharin were added in an equal ratio to give a 0.5 wt % solution, the viscosity of the cream was reduced to 22,000 mPa·s. When maltol and sodium saccharin were dissolved in an equal ratio at 2 wt %, the viscosity of the cream was reduced to 11,000 mPa·s. By comparison, when ascorbic acid-2-glucoside (AA2G) was added to make a 0.5 wt % cream, the viscosity of the resulting cream increased to 26,000 mPa·s. These results are as shown in FIG. 6.

This test showed that the addition of maltol and sodium saccharin from 0.5 wt % onward reduced the viscosity of the cream as opposed to an addition with 2% AA2G. A significant drop in viscosity was observed upon increasing the amount of maltol and sodium saccharin up to 2 wt %. A reduced viscosity (creamy in texture) provides an advantage to ensure proper dispersal, and easy application and absorption of the cream on skin. Further, it also provides flexible formulatory advantage since a reduced viscosity allows for the possibility of the addition of more active compounds or functional ingredients (e.g. emulsifiers, emollients, etc.)

Example 11

A blend containing 0.25% maltol and 0.25% sodium saccharin (NZW 06) was successfully incorporated into the following commercial skin lightening cum anti-ageing formulation, containing water, cyclopentasiloxane, ethylhexyl methoxycinnamate, 4-methylbenzylidene camphor, ceteareth-12, glycerin, cetyl alcohol, polymethyl metacrylate, diisopropyl sebacate, isodecyl neopentanoate, lauryl lactate, glyceryl stearate, PEG-100 Stearate, Vitis vinifera (Grape) seed oil, carbomer, phenoxyethanol, butyl methoxydibenzoylmethane, tocopheryl acetate, triethanolamine, parfum (fragrance), chlorphenesin, hydrolysed wheat protein, tetrasodium EDTA, magnesium aspartate, zinc gluconate, BHT, Faex extract (Yeast extract), benzyl salicylate, hydroxyisohexyl 3-cyclohexene carboxaldehyde, copper gluconate, hexyl cinnamal, methylisothiazolinone, sodium hyaluronate, ethylhexylglycerin, linalool, alpha-isomethyl ionone, sodium chloride, geraniol, limonene, butylphenyl methylpropional, with no change to the colour, consistency, or physical appearance to the formulation.

Example 12

A blend containing 0.25% maltol and 0.25% sodium saccharin (NZW 06) was successfully incorporated into the following two commercial skin lightening formulations with no change to the colour, consistency, or physical appearance to the formulation:
(i) Commercial skin lightening formulation containing water, palmitic acid & stearic acid, niacinamide, glycerin, cetearyl ethylhexnoate and isopropyl myristate, ethylhexyl methoxycinnamate, butylmethoxydibenzoylmethane, hydroxystearic acid, sodium ascorbyl phosphate, tocopheryl acetate, allantoin, pyridoxine hydrochloride, cetyl alcohol, dimethicone, titanium dioxide and aluminium hydroxide and stearic acid, phenoxyethanol, methylparaben, propylparaben, potassium hydroxide, titanium dioxide and dimethicone, disodium EDTA, CI77491, isopropyl titanium triisostearate, triethoxysilylethyl polydimethylsiloxyethyl dimethicone, CI 15510, CI 17200, and Perfume;
(ii) Commercial skin lightening formulation containing water, stearic acid, ethylhexyl methoxycinnamate, glycerine, isopropyl myristate, niacinamide, fragrance, potassium hydroxide, phenoxyethanol, methylisothiazolinone, cetyl alcohol, coco caprylate/caprate, butyl methoxydibenzoylmethane, Crocus sativus flower extract, titanium dioxide (and) caprylic/capric triglyceride (and) polyhydroxystearic acid (and) alumina, acrylates/C10-30 alkyl acrylate crosspolymer, disodium EDTA, tocopheryl acetate, Medicago sativa extract, and CI 15985.

Example 13

A blend containing 0.25% maltol and 0.25% sodium saccharin (NZW 06) was successfully incorporated into the following commercial anti-ageing formulation comprising octinoxate 7.5%, oxybenzone 5.0%, octisalate 5.0%, octocrylene 2.2%, avobenzone 2.0%; Inactive Ingredients: water, dimethicone, C12-15 alkyl benzoate, butylene glycol, cyclopentasiloxane, isostearyl neopentanoate, Theobroma cacao (Cocoa) seed butter, dimethicone/vinyl dimethicone crosspolymer, Butyrospermum parkii (Shea butter) extract, Ppg-2 Isoceteth-20 Acetate, glycerol, caprylic/capric triglyceride, ceramide 1, ceramide 3, ceramide 6, *Alpinia speciosa* leaf extract, Hibiscus abelmoschuss seed extract, *Trifolium pratense* (clover) flower extract, sodium hyaluronate, ascorbyl palmitate, retinyl linoleate, retinyl palmitate, tocopherol, tocopheryl acetate, cetearyl dimethicone crosspolymer, isohexadecane, acetyl octapeptide-3, propylene glycol, sodium PCA, trehalose, urea, hydrogenated lecithin, lecithin, phospholipids, phytosphingosine, polyphosphorylcholine glycol acrylate, sucrose, cetearyl alcohol, cholesterol, sodium lauroyl lactylate, hydroxyethyl acrylate/sodium acryloyldimethyl taurate copolymer, polysorbate 80, trideceth-6, acrylamide/sodium acrylate copolymer, polyquaternium-51, PEG-8, acrylates/C10-30 alkyl acrylate crosspolymer, carbomer, xanthan gum, sodium hydroxide, BHT, mineral oil/paraffinum liquidum/huile minérale, dimethiconol, phenyl trimethicone, partum/fragrance, alpha-isomethyl ionone, benzyl benzoate, butylphenyl methylpropional, citral, citronellol, eugenol, geraniol, hexyl cinnamal, hydroxyisohexyl 3-cyclohexene carboxaldehyde, limonene, linalool, benzoic acid, butylparaben, ethylparaben, isobutylparaben, methylparaben, phenoxyethanol, potassium sorbate, propylparaben, chlorphenesin, Red 4 (Ci 14700) and Yellow 6 (Ci 15985).

Example 14

Multiple serum formulations which may be used in single or multi-use cosmetic forms such as capsules or in jar or in tube containers were prepared as follows:
a) Water 96.3%, 3% of a blended powder (containing 10% Maltol and 90% Sodium Saccharin), 0.6% xanthan gum, 0.1% DS-Hydroceramide 50.
b) Water 96.3%, 3% of a blended powder (containing 9.9% Maltol, 89.5% Sodium Saccharin, 0.6% Menthol), 0.6% xanthan gum, 0.1% DS-Hydroceramide 50.
c) Water 96.3%, 1.5% of a blended powder (containing 9.9% Maltol, 89.5% Sodium Saccharin, 0.6% Menthol), 0.6% xanthan gum, 0.1% DS-Hydroceramide 50.
d) Water 96.3%, 6% of a blended powder (containing 9.9% Maltol, 89.5% Sodium Saccharin, 0.6% Menthol), 0.6% xanthan gum, 0.1% DS-Hydroceramide 50.

Example 15

A cream containing multiple active ingredients was prepared as follows:

Acesulphame K, sodium saccharin, maltol, dehydroacetic acid and theobromine each at a concentration of 0.25% were blended together into a base cream. The cream base used for blending the active ingredients contained the ingredients as follows: Aqua, disodium EDTA, Ultrez-20, glycerin, methyl gluceth-20, PEG-20 methyl glucose sesquistearate, isopropyl isostearate/isopropyl myristate, Tween 20, and NaOH. The cream base was white in colour, with a pH ranges between 6 and 7. The resultant blended cream was even, smooth and had superior skin feel as compared to the original unblended cream base.

Example 16

A cream containing 0.5% sodium saccharin, 0.5% maltol and 2% zinc oxide was prepared as follows:

0.05% of Disodium EDTA was added to 78.55% water and stirred until fully dissolved. 0.5% of Ultrez 20 was added to the mixture while the mixture was continuously stirred. 2% glycerin, 1% methyl gluceth-20, 0.75% PEG-20 methyl glucose sesquistearate, 0.5% maltol, 0.5% sodium saccharin were then added, while the mixture was heated to 70-80° C. with constant stirring. An oil phase was prepared by blending 10 g of petrolatum/beeswax/petroleum jelly blend containing 2% zinc oxide, 0.5% methyl glucose sesquisterate, 4% isopropyl myristate and 1.65% Tween 20 together while the blend was heated to a temperature of 70-80° C. Once the temperatures of the two phases were equal, the two phases were combined and stirred until the temperature of the mixture dropped to 60° C. pH of the mixture was then adjusted to between pH 6 and 7 with sodium hydroxide.

Example 17

In-vivo skin lightening study on 83 Indian female subjects (who were divided into four groups) and monitored by self-assessment, assessment by dermatologists, and instrumentally was carried out. This double-blind Clinical Research Organisation (CRO) study proved the efficacy of skin lightening and skin quality among four test products. Group A subjects tested a commercially available market sample in cream base (TP3M). Group B subjects tested a pink water gel moisturiser chassis with 0.5% Maltol and 0.5% Sodium Saccharin post-added into the gel (TP21). Group C subjects tested the pink water gel moisturiser chassis of the same composition as in Group B as a placebo, with no other actives post-added. (TP4P). Group D subjects tested the pink water gel moisturiser chassis of the same composition as in Group C with 3% Niacinamide post-added into the gel (TP13). A cream of the same composition, but containing 3.0% niacinamide (TP13, Table VIII) instead of maltol and saccharin was used as a positive control.

The Pink Water Gel Moisturiser Chassis as used in TP21, TP4P and TP13 is defined as containing the following ingredients (as per their US INCI Name): Dimethicone, Hydrogenated Polydecene, Pentaerythrityl tetraisostearate, DC 1403 (Dimethicone; Dimethiconol), Tocopheryl Acetate, Water, Disodium EDTA, Glycerin, Butylene Glycol, Pentylene Glycol, Sodium Hyaluronate, Xanthan gum, Carbomer, Methylparaben, Sodium hydroxide, Rose Damascena Organic Distillate 1:20 SB 721033 (Rosa Damascena Flower Water; Citric Acid, Water, Sodium Benzoate; Potassium Sorbate), Honey, Phenoxyethanol, Fragrance, Colorant. Niacinamide and the 1% Maltol and Sodium Saccharin mixture was respectively post-added into the pink water gel moisturiser chassis.

The commercially available market sample in cream base labelled TP3M is defined as containing the following active ingredients: Water, stearic acid, niacinamide, glycerin, cetearyl ethylhexanoate, ethylhexyl methoxycinnamate, titanium dioxide, cetyl alcohol, dimethicone, potassium hydroxide, butylmethoxydibenzoylmethane, perfume, tocopheryl acetate, sodium ascorbyl phosphate, phenoxyethanol, methylparaben, allantoin, propylparaben, hydroxystearic acid, isopropyl myristate, disodium EDTA, aluminium hydroxide, triethoxysilylethylpolydimethylsiloxyethyl dimethicone, dimethicone, isopropyl titanium triisostearate, pyridoxine hydrochloride, BHT, CI 77491, CI 17200, CI 15510.

The subjects were recruited and selected according to inclusion and exclusion criteria, as well as the prohibition and restriction concepts defined in the study protocol. In this study, 83 female subjects were included by the Investigator. The age of the subjects was between 18-25 years old with the average age of each of the four groups being 21.3, 21.41, 20.83, and 21.35 years respectively.

The selected subjects were treated on the entire face with the tested products. Subjects were briefed on how to use the tested products which they were required to use by themselves over the 56 days. The subjects were instructed to avoid direct facial sun exposure throughout the course of the study. Test subjects were also told to abstain from using new skincare products or cosmetic products, or change their existing brands, before and during the course of the clinical study.

Before application of the tested product, the skin melanin index was measured at all tested sites of the cheeks in each subject. The tested product was applied twice daily, once in the morning and once in the evening, over 56 days on the entire face. During this period, the subjects were monitored for their usage of the product every week in three ways:—

Skin melanin index was measured after 7, 14, 28 and 56 days of application. Three measurements were determined at the same site using Mexameter MX 18 and Chromameter, and the mean value was calculated. In addition, the subjects were asked to assess their skin and score the skin attributes as per self-assessment questionnaire on Day 0, Day 7, Day 14, Day 28 and Day 56. The investigators were also asked to make observations each time the subject visited the clinic (i.e. on Day 7, 14, 21, 28, ad 56). The average data from all measurements was statistically analysed using the paired t test using R software to give results in three forms:— a. A skin melanin index for each test site (corresponding to each test product) on D0, D7, D14, D28, and D56
b. A comparison result between the test products and the positive control, and
c. A comparison between the test products; which were found to be statistically significant at p<0.05 levels.

The main conclusions were that cream formulations containing maltol and sodium saccharin at an amount of 1% w/w were equally active in lightening the skin of the subjects as compared to the positive control formulation containing 3.0% w/w niacinamide. The cream containing a blend of 0.5% maltol and 0.5% saccharin (TP21) was preferred by the subjects, and the sample containing the 3.0% niacinamide (TP13) was least preferred (See Table XVI).

Using the sample containing maltol and saccharin (TP21), 95% of the subjects observed and reported lightening of their skin by day 7 of the trial. This result was confirmed when skin melanin index measurements were made using a Mexameter as the sample containing the blend of 0.5% maltol and 0.5% saccharin (TP21) had specific activities 8.4 fold higher than the sample containing 3% niacinamide (TP13) after use for 7 days, and 4.6 fold greater when used for 14 and 28 days, and with these results statistically significant at p<0.05 levels (See Table XIV).

Tables XII to XIII illustrate the skin lightening effects of the various compositions by measuring the difference of skin melanin index (SMI) at day 14 and day 56. Table XIV shows the specific activities obtained for TP21 and TP13 and how they compare against each other. Table XV shows the method of applying the cosmetic product containing the cosmetic composition. As shown in Table XIII, the results of TP21 consistently yielded comparable or better SMI reduction as compared to the 3 other compositions (TP3M, TP4P, TP13) after 56-day applications. This statistically shows the superior specific activity of the products containing maltol and sodium saccharin in only an amount of 1% Maltol and Sodium Saccharin, as compared to 3 wt % Niacinamide in TP13.

From these results, the cosmetic composition in TP21 was calculated to offer a 2-fold cost-in-use advantage as compared to niacinamide.

TABLE XII

Skin Melanin Index for Products Compared To Baseline

| Group | Product Code | Product | Baseline | Skin Melanin Index (unit)^ After 7 Days application | After 14 Days application | After 28 Days application | After 56 Days application |
|---|---|---|---|---|---|---|---|
| A (N = 20) | TP3M | Cream base containing Niacinamide at 1.21% (amongst other actives as measured externally via HPLC) | 443.12 ± 127.83 | 434.1 ± 133.19 | 433.18 ± 136.08 | 431.40 ± 132.43 | 426.11 ± 143.61 |
| B (N = 20) | TP21 | Cream base containing Sodium Saccharin at 0.5% and Maltol at 0.5% | 492.90 ± 104.81 | 482 ± 104.03 | 483.88 ± 106.70 | 480.04 ± 100.74 | 470.47 ± 96.14 |
| C (N = 22) | TP4P | Gel Chassis (control) | 443.39 ± 97.86 | 437.67 ± 95.95 | 439.23 ± 95.03 | 436.14 ± 95.47 | 430.40 ± 92.22 |
| D (N = 21) | TP13 | Cream base containing Niacinamide at 3% | 450.10 ± 116.15 | 446.26 ± 117.84 | 440.41 ± 118.43 | 441.85 ± 117.45 | 440.13 ± 117.11 |

TABLE XIII

Improvement In Skin Melanin Index For TP21 Containing 0.5% Maltol & 0.5% Sodium Saccharin compared against TP3M, TP4P and TP13

| Group | Product Code | Product | Baseline | Skin Melanin Index (unit)^ After 7 Days application | After 14 Days application | After 28 Days application | After 56 Days application |
|---|---|---|---|---|---|---|---|
| A (N = 20) | TP3M | Cream base containing Niacinamide at 1.21% (amongst other actives as measured externally via HPLC) | 443.12 ± 127.83 | −9.02 ± 15.79 | −9.93 ± 18.42 | −11.72 ± 20.26 | −17.01 ± 15.78 |
| B (N = 20) | TP21 | Cream base containing Sodium Saccharin at 0.5% and Maltol at 0.5% | 492.90 ± 104.81 | −10.73 ± 9.57 | −9.02 ± 14.46 | −12.86 ± 13.81 | −22.43 ± 8.67 |
| C (N = 22) | TP4P | Gel Chassis (control) | 443.39 ± 97.86 | −5.71 ± 12.77 | −4.16 ± 21.16 | −7.24 ± 22.31 | −12.99 ± 5.64 |
| D (N = 21) | TP13 | Cream base containing Niacinamide at 3% | 450.10 ± 116.15 | −3.83 ± 9.58 | −5.85 ± 11.04 | −8.25 ± 15.19 | −9.97 ± 0.96 |

Specific activity has been obtained as follows. Specific activity is the skin melanin index (SMI) reduction per gram of accumulated actives applied at a time point. It has been calculated in the following manner;

$$\text{Specific activity} = \frac{\Delta SMI\ T_x}{\Sigma\ \text{Active Compound}_{mg}\ T_x}.$$

TABLE XIV

Specific Activity For TP21 as compared against TP13 at Day 7, 14 and 28

| | | | Skin Melanin Index (unit)^ | | | | | |
|---|---|---|---|---|---|---|---|---|
| | | | Day 7 | | Day 14 | | Day 28 | |
| Group | Product Code | Product | Accumulated actives applied (g) | Specific Activity | Accumulated actives applied (g) | Specific Activity | Accumulated actives applied (g) | Specific Activity |
| B (N = 20) | TP21 | Cream base containing Sodium Saccharin at 0.5% and Maltol at 0.5% | 0.084 | 127.74 ± 113.93 | 0.168 | 53.68 ± 86.06 | 0.336 | 38.27 ± 41.10 |
| D (N = 21) | TP13 | Cream base containing Niacinamide at 3% | 0.252 | 15.21 ± 38.03 | 0.504 | 11.61 ± 21.9 | 1.01 | 8.16 ± 15.04 |

TABLE XV

Method of Applying the Products Containing the Cosmetic Composition

| | |
|---|---|
| Application Area | Whole face |
| Quantity Applied | A quantity equivalent to 1 mg/cm2 of sample to be applied onto whole face at each application. (i.e. 2 mg/cm2 daily). As such, a quantity ranging between 0.5 g to 0.6 g should be applied on the face at each application, with a range of 1 to 1.2 g per day. |
| Concentration Applied | As per the product issued to the subject |
| Frequency | Twice daily, morning and evening Note: if subject showers in the morning or evening, application of test material should always be done after shower |
| Usage | Apply each product on entire face |
| Duration of Application | 56 Days |

Table XI illustrates the percentage of subjects who were satisfied with the products from Day 7 to Day 28.

TABLE XVI

Results of user satisfaction measurements after applying various products

Q: Are you satisfied with the quality of skin lightening achieved?
A: Choose 1: Very Satisfied, Satisfied, Average, Not Satisfied

| Product | Day 7 | Day 14 | Day 28 |
|---|---|---|---|
| TP3M | 85 | 75 | 80 |
| TP21 | 76 | 90 | 85 |
| TP4P | 68 | 77 | 82 |
| TP13 | 62 | 57 | 80 |

Q: If this product would be available on the market, would you use it?
A: Yes/No

| Product | % Yes | % No |
|---|---|---|
| TP3M | 95 | 5 |
| TP21 | 100 | 0 |
| TP4P | 91 | 9 |
| TP13 | 90 | 10 |

Although the foregoing invention has been described in some detail by way of illustration and example, and with regard to one or more embodiments, for the purposes of clarity of understanding, it is readily apparent to those of ordinary skill in the art in light of the teachings of this invention that certain changes, variations and modifications may be made thereto without departing from the scope of the invention.

It should be appreciated by the person skilled in the art that variations and combinations of features described above, not being alternative or substitutes, may be combined to form yet further embodiments falling within the intended scope of the invention.

The invention claimed is:

1. A cosmetic skin lightening composition comprising:
two or more compounds selected from the group consisting of sodium saccharin, maltol and theobromine having the following structures:

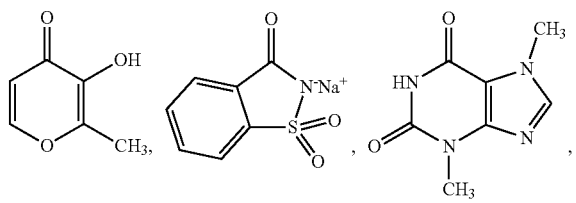

or their salts, in a combination selected from the group consisting of:
  i. maltol and sodium saccharin in a weight ratio of 1:1 and;

ii. maltol, sodium saccharin and theobromine in a weight ratio of 1:2:0.6
wherein the composition is to be topically applied to the skin of a subject for lightening of the skin.

2. The cosmetic skin lightening composition according to claim 1, wherein the composition comprises maltol in an amount of 0.01 to 10 wt % based on the total weight of the composition.

3. The cosmetic skin lightening composition according to claim 1, wherein the composition comprises sodium saccharin in an amount of 0.01 to 20 wt % based on the total weight of the composition.

4. The cosmetic skin lightening composition according to claim 1, wherein each of the two or more compounds is provided in the form of an extract derived from a plant material or yeast.

5. The cosmetic skin lightening composition according to claim 1, wherein the maltol and/or theobromine is provided in the form of an extract derived from a plant material or yeast.

6. The cosmetic skin lightening composition according to claim 1, wherein the composition further comprises a zinc or copper cation forming a hetero-dimer of the two or more compounds.

7. The cosmetic skin lightening composition according to claim 1, wherein the lightening of the skin includes reducing endogenous and/or UV-induced melanogenesis; reducing activities of melanogenesis metabolic pathway and/or one or more of the signalling pathways that control the activity of the melanogenesis metabolic pathway; reducing the melanin content of the skin of a subject; lightening of the skin, pigmented spots, freckles, blemishes and dark circles around the eyes of the subject.

8. The cosmetic skin lightening composition according to claim 1, wherein the two or more compounds have antibacterial properties and viscosity reducing properties when formulated into the composition.

9. A cosmetic method for skin lightening comprising topically applying an effective amount of the cosmetic composition as claimed in claim 1 on the skin of a subject, for lightening of skin.

10. The cosmetic method of claim 9, wherein the lightening of the skin is selected from reducing endogenous and/or UV-induced melanogenesis; reducing activities of melanogenesis metabolic pathway and/or one or more of the signalling pathways that control the activity of the melanogenesis metabolic pathway; or reducing the melanin content of the skin of a subject.

11. The cosmetic method according to claim 9, wherein the lightening of the skin is selected from lightening pigmented spots, freckles, blemishes or dark circles around the eyes of the subject.

* * * * *